United States Patent
Ebenstein et al.

(10) Patent No.: US 12,043,863 B2
(45) Date of Patent: *Jul. 23, 2024

(54) DETECTION OF HYDROXYMETHYLCYTOSINE BASES

(71) Applicant: Ramot at Tel-Aviv University Ltd., Tel-Aviv (IL)

(72) Inventors: Yuval Ebenstein, Tel Aviv (IL); Micha Fridman, Tel Aviv (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 240 days.

This patent is subject to a terminal disclaimer.

(21) Appl. No.: 17/400,168

(22) Filed: Aug. 12, 2021

(65) Prior Publication Data

US 2021/0371906 A1 Dec. 2, 2021

Related U.S. Application Data

(60) Continuation of application No. 16/424,523, filed on May 29, 2019, now Pat. No. 11,091,793, which is a
(Continued)

(51) Int. Cl.
*C12Q 1/6806* (2018.01)
*C12P 19/30* (2006.01)
*G01N 21/64* (2006.01)

(52) U.S. Cl.
CPC .......... *C12Q 1/6806* (2013.01); *C12P 19/305* (2013.01); *G01N 21/6428* (2013.01)

(58) Field of Classification Search
CPC .................. C12Q 2537/164; C12Q 1/6827
See application file for complete search history.

(56) References Cited

U.S. PATENT DOCUMENTS

| 5,489,507 A | 2/1996 | Chehab |
| 5,750,345 A | 5/1998 | Bowie |

(Continued)

FOREIGN PATENT DOCUMENTS

| WO | WO 2011/127136 | 10/2011 |
| WO | WO 2012/031029 | 3/2012 |

(Continued)

OTHER PUBLICATIONS

Official Action Dated Jul. 11, 2023 from the US Patent and Trademark Office Re. U.S. Appl. No. 15/775,015. (18 pages).
(Continued)

*Primary Examiner* — Joseph G. Dauner

(57) ABSTRACT

Provided herein is a method of labeling the epigenetic modification 5-hydroxymethyl-cytosine along a DNA molecule that involves attaching a 5-hydroxymethyl-cytosine specific labeling agent to the DNA molecule, which is effected by enzymatically synthesizing UDP-6-N3-Glucose by subjecting 6-azidoglucose to an enzymatic catalysis by N-acetylhexoseamine 1-kinase (NahK) in the presence of ATP to thereby obtain a phosphorylated 6-azidoglucose, followed by subjecting the phosphorylated 6-azidoglucose to enzymatic catalysis by uridyltransferase (GlmU) in the presence of UTP to thereby obtain UDP-6-N3-Glucose, followed by incubating the DNA molecule with UDP-6-N3-Glucose and ß-glucosyltransferase, to thereby obtain a 5-hydroxymethyl-cytosin e glycosylated by a 6-azidoglucose residue in the DNA molecule, and reacting the modified DNA molecule with a labeling agent which is chemically compatible with the azide group of the 6-azidoglucose residue.

19 Claims, 9 Drawing Sheets
(6 of 9 Drawing Sheet(s) Filed in Color)
Specification includes a Sequence Listing.

Related U.S. Application Data division of application No. 14/894,350, filed as application No. PCT/IL2014/050010 on Jan. 5, 2014, now Pat. No. 10,351,898.

(60) Provisional application No. 61/828,129, filed on May 28, 2013.

(56) References Cited

U.S. PATENT DOCUMENTS

| | | |
|---|---|---|
| 5,929,227 A | 7/1999 | Glazer et al. |
| 8,206,935 B2 | 6/2012 | Li et al. |
| 8,741,567 B2 | 6/2014 | He et al. |
| 9,115,386 B2 | 8/2015 | Rao et al. |
| 9,447,452 B2 | 9/2016 | Rao et al. |
| 10,351,898 B2 | 7/2019 | Ebenstein et al. |
| 10,718,010 B2 | 7/2020 | Song et al. |
| 2003/0082551 A1 | 5/2003 | Zarling et al. |
| 2003/0113755 A1 | 6/2003 | Nishigaki et al. |
| 2004/0152084 A1 | 8/2004 | Slattum et al. |
| 2010/0015607 A1 | 1/2010 | Geiss et al. |
| 2010/0143929 A1 | 6/2010 | Levenson et al. |
| 2011/0236894 A1 | 9/2011 | Rao et al. |
| 2011/0301045 A1 | 12/2011 | He et al. |
| 2012/0003663 A1 | 1/2012 | Li et al. |
| 2012/0107808 A1 | 5/2012 | Li et al. |
| 2012/0122087 A1 | 5/2012 | Li et al. |
| 2013/0177912 A1 | 7/2013 | Rao et al. |
| 2014/0030727 A1 | 1/2014 | Pfeiffer |
| 2014/0038183 A1 | 2/2014 | Yegnasubramanian et al. |
| 2014/0080715 A1 | 3/2014 | Lo et al. |
| 2014/0240695 A1 | 8/2014 | Pagan et al. |
| 2014/0322707 A1 | 10/2014 | He et al. |
| 2015/0056616 A1 | 2/2015 | He et al. |
| 2016/0115525 A1 | 4/2016 | Ebenstein et al. |
| 2017/0145484 A1 | 5/2017 | Rao et al. |
| 2017/0168043 A1 | 6/2017 | Rao et al. |
| 2017/0175085 A1 | 6/2017 | Rao et al. |
| 2017/0176420 A1 | 6/2017 | Rao et al. |
| 2017/0176421 A1 | 6/2017 | Rao et al. |
| 2017/0298422 A1 | 10/2017 | Song et al. |
| 2018/0327855 A1 | 11/2018 | Ebenstein et al. |
| 2019/0017109 A1 | 1/2019 | Song et al. |
| 2019/0316178 A1 | 10/2019 | Ebenstein et al. |
| 2020/0277666 A1 | 9/2020 | Song et al. |

FOREIGN PATENT DOCUMENTS

| | | |
|---|---|---|
| WO | WO 2013/188436 | 12/2013 |
| WO | WO 2014/152279 | 9/2014 |
| WO | WO 2014/191981 | 12/2014 |
| WO | WO 2017/081689 | 5/2017 |

OTHER PUBLICATIONS

Advisory Action Before the Filing of An Appeal Brief Dated Apr. 19, 2018 From the US Patent and Trademark Office Re. U.S. Appl. No. 14/894,350. (6 pages).
Communication Pursuant to Article 94(3) EPC Dated Jun. 8, 2021 From the European Patent Office Re. Application No. 16863787.4. (4 Pages).
Communication Pursuant to Article 94(3) EPC Dated Jul. 24, 2020 From the European Patent Office Re. Application No. 16863787.4. (6 Pages).
Final Official Action Dated Apr. 13, 2020 from the US Patent and Trademark Office Re. U.S. Appl. No. 15/775,015. (39 pages).
Final Official Action Dated May 20, 2021 From the US Patent and Trademark Office Re. U.S. Appl. No. 15/775,015. (16 Pages).
Grounds of Reasons for Rejection Dated Jul. 31, 2020 From the Korean Intellectual Property Office Re. Application No. 10-2015-7036584 and Its Translation Into English. (14 Pages).
International Preliminary Report on Patentability Dated Dec. 10, 2015 From the International Bureau of WIPO Re. Application No. PCT/IL2014/050010.
International Preliminary Report on Patentability Dated May 24, 2018 From the International Bureau of WIPO Re. Application No. PCT/IL2016/051218. (10 Pages).
International Search Report and the Written Opinion Dated May 4, 2014 From the International Searching Authority Re. Application No. PCT/IL2014/050010.
International Search Report and the Written Opinion Dated Jan. 31, 2017 From the International Searching Authority Re. Application No. PCT/IL2016/051218.(14 pages).
Interview Summary Dated Nov. 2, 2020 From the US Patent and Trademark Office Re. U.S. Appl. No. 15/775,015. (4 Pages).
Notice of Allowance Dated Mar. 6, 2019 From the US Patent and Trademark Office Re. U.S. Appl. No. 14/894,350. (8 Pages).
Notice of Allowance Dated Apr. 14, 2021 From the US Patent and Trademark Office Re. U.S. Appl. No. 16/424,523. (14 Pages).
Official Action Dated Nov. 10, 2020 from the US Patent and Trademark Office Re. U.S. Appl. No. 15/775,015. (27 pages).
Official Action Dated Oct. 10, 2019 From the US Patent and Trademark Office Re. Application No. 151775,015. (35 pages).
Official Action Dated May 16, 2017 From the US Patent and Trademark Office Re. U.S. Appl. No. 14/894,350. (20 pages).
Official Action Dated Nov. 22, 2017 From the US Patent and Trademark Office Re. U.S. Appl. No. 14/894,350. (13 pages).
Official Action Dated Sep. 28, 2018 From the US Patent and Trademark Office Re. U.S. Appl. No. 14/894,350. (7 pages).
Official Action Dated Sep. 29, 2020 from the US Patent and Trademark Office Re. U.S. Appl. No. 16/424,523. (21 pages).
Requisition by the Examiner Dated Jan. 24, 2020 From the Innovation, Science and Economic Development Canada, Canadian Intellectual Property Office Re. Application No. 2,912,666. (13 Pages).
Requisition by the Examiner Dated Aug. 31, 2020 From the Innovation, Science and Economic Development Canada, Canadian Intellectual Property Office Re. Application No. 2,912,666. (8 Pages).
Restriction Official Action Dated Mar. 24, 2017 From the US Patent and Trademark Office Re. U.S. Appl. No. 14/894,350. (12 Pages).
Restriction Official Action Dated May 29, 2019 From the US Patent and Trademark Office Re. U.S. Appl. No. 15/775,015. (7 Pages).
Supplementary European Search Report and the European Search Opinion Dated May 27, 2019 From the European Patent Office Re. Application No. 16863787.4. (10 Pages).
Cai "A Chemoenzymatic Route to Unnatural Sugar Nucelotides and Their Applications and Enzymatic Synthesis of Rare Sugars With Aldolases In Vitro and In Vivo", Dissertation, Presented in Partial Fulfillment of the Requirements for the Degree Doctor of Philosophy, Graduate School of The Ohio State University, p. 1-353, 2011. Schemes 2.3, 2.12, 2.13, 2.14, p. 47, Para 2.3.1, Table 2.4, 2.5.
Cai et al. "Genome-Wide Mapping of 5-Hydroxymethylcytosines in Circulating Cell-Free DNA as a Non-Invasive Approach for Early Detection of Hepatocellular Carcinoma," Gut 68: 2195-2205, 2019.
Chen et al. "Quantification of 5-Methylcytosine and 5-Hydroxymethylcytosine in Genomic DNA From Hepatocellular Carcinoma Tissues by Capillary Hydrophilic-Interaction Liquid Chromatography/Quadrupole Time-of-Flight Mass Spectrometry", Clinical Chemistry, 59(5): 824-832, Published Online Jan. 23, 2013.
Chowdhury et al. "Quantification of 5-Methylcytosine, 5-Hydroxymethylcytosine and 5-Carboxylcytosine from the Blood of Cancer Patients by an Enzyme-Based Immunoassay", Analytica Chimica Acta, 852:212-217, Dec. 10, 2014.
Cortese et al. "Epigenetic Markers of Pprostate Cancer in Plasma Circulating DNA," Human Molecular Genetics 21(16): 3619-3631, 2012.
Diaz et al. "Liquid Biopsies: Genotyping circulating Tumor DNA," Journal of Clinical Oncology 32(6): 579-586, 2014.
Gallagher "Quantification of DNA and RNA with Absorption and Fluorescence Spectroscopy", Current Protocols in Cell Biology, A.3D.1-A.3D.8, May 1, 2001.

(56) References Cited

OTHER PUBLICATIONS

Grelus et al. "Clinical Significance of Measuring Global Hydroxymethylation of White Blood Cell DNA in Prostate Cancer: Comparison to PSA in a Pilot Exploratory Study", International Journal of Molecular Sciences, 18(2465): 1-10, Nov. 2017.
Haffner et al. "Global 5-Hydroxymethylcytosine Content Is Significantly Reduced in Tissue Stem/Progenitor Cell Compartments and in Human Cancers", Oncotarget, 2(8): 627-637, Sep. 2, 2011.
Ju et al. "Fluorescence Energy Transfer Dye-labeled Primers for DNA Sequencing and Analysis", Proc. Natl. Acad. Sci USA, Biophysics, 92:4347-4351, May 9, 1995.
Ko et al. "TET Proteins and 5-Methylcytosine Oxidation in Hematological Cancers", Immunological Reviews, 263(1): 6-21, Jan. 2015.
Konstandin et al. "Genomic 5-Hydroxymethylcytosine Levels Correlate with TET2 Mutations and a Distinct Global Gene Expression pattern in Secondary Acute Myeloid Leukemia", Leukemia 25: 1649-1652, 2011.
Kowalik et al. "Current Approaches for Avoiding the Limitations of Circulating Tumor Cells Detection Methods—Implications for Diagnosis and Treatment of Patients with Solid Tumors", Translational Research, 185:58-84.e15, Jul. 2017.
Levy-Sakin et al. "Beyond Sequencing: Optical Mapping of DNA in the Age of Nanotechnology and Nanoscopy", Current Opinion in Biotechnology, 24(4): 690-698, Published Online Feb. 18, 2013. p. 692, Right Col., Last Para.
Levy-Sakin et al. "Imaging of Individual Modified Bases on Genomic DNA: Towards Single Molecule Epigenetic Optical Mapping", Poster, presented on Jan. 10, 2013 in a closed meeting of single molecule experts in Aspen, Colorado.
Li et al. "Distribution of 5-Hydroxymethylcytosine in Different Human Tissues", Journal of Nucleic Acids, 2011: ID 870726, 6 Pages, Apr. 15, 2011.
Lim et al. "DNA Methylation Profiling in Nanochannels", Biomicrofluidics, 5(3): 034106-1-034106-8, Published Online Jul. 25, 2011.
Michaeli et al. "Optical Detection of Epigenetic Marks: Sensitive Quantification and Direct Imaging of Individual Hydroxymethylcystosine Bases", Chemical Communications, XP055589031, 49(77): 8599-8601, Oct. 7, 2013.
Michaeli et al. "Optical Detection of Epigenetic Marks: Sensitive Quantification and Direct Imaging of Individual Hydroxymethylcytosine Bases", Chemical Communications, 49(77): 8599-8601, Oct. 7, 2013.
Nifker et al. "One-Pot Chemoenzymatic Cascade for Labeling of the Epigenetic Marker 5-Hydroxymethylcytosine", ChemBioChem, XP055589051, 16(13): 1857-1860, Published Online Jul. 27, 2015.
Nifker et al. "Supporting Information: One-Pot Chemoenzymatic Cascade for Labeling of the Epigenetic Marker 5-Hydroxymethylcytosine", ChemBioChem, XP055589051, 16(13): 1857-1860, 2015.
Shahal et al. "Spectroscopy Quantification of 5-Hydroxymethylcystosine in Genomic DNA", Analytical Chemistry, XP055589033, 86(16): 8231-8237, Published Online Jul. 11, 2014.
Sidorova et al. "Microfluidic-Assisted Analysis of Replicating DNA Molecules", Nature Protocols, 4(6): 849-861, May 14, 2009.
Song et al. "5-Hydroxymethylcytosine Signatures in Cell-Free DNA Provide Information about Tumor Types and Stages," Cell Research 27(10): 1231-1242, 2017.
Song et al. "Selective Chemical Labeling Reveals the Genome-Wide Distribution of 5-Hydroxymethylcytosine", Nature Biotechnology, 29(1): 68-75, Jan. 2011.
Song et al. "Simultaneous Single-Molecule Epigenetic Imaging of DNA Methylation and Hydroxymethylation," PNAS 113(16): 4338-4343, 2016.
Szulwach et al. "Integrating 5-Hydroxymethylcytosine Into the Epigenomic Landscape of Human Embryonic Stem Cells", PLoS Genetics, 7(6): e1002154-1-e1002154-13, Jun. 23, 2011.
Tu et al. "'Testing your Methyl': DNA Methylation Profiling of Serum DNA of HCC Patients," Hepatology International 7: 785-878, 2013.
Zhang et al. "Tet-Mediated Covalent Labelling of 5-Methylcytosine for its Genome-Wide Detection and Sequencing," Nature Communications 4: Article No. 1517, 2013, 10 pages.
Official Action Dated Nov. 9, 2022 from the US Patent and Trademark Office Re. U.S. Appl. No. 15/775,015. (25 pages).
Communication Pursuant to Article 94(3) EPC Dated Aug. 18, 2023 From the European Patent Office Re. Application No. 16863787.4 (3 Pages).

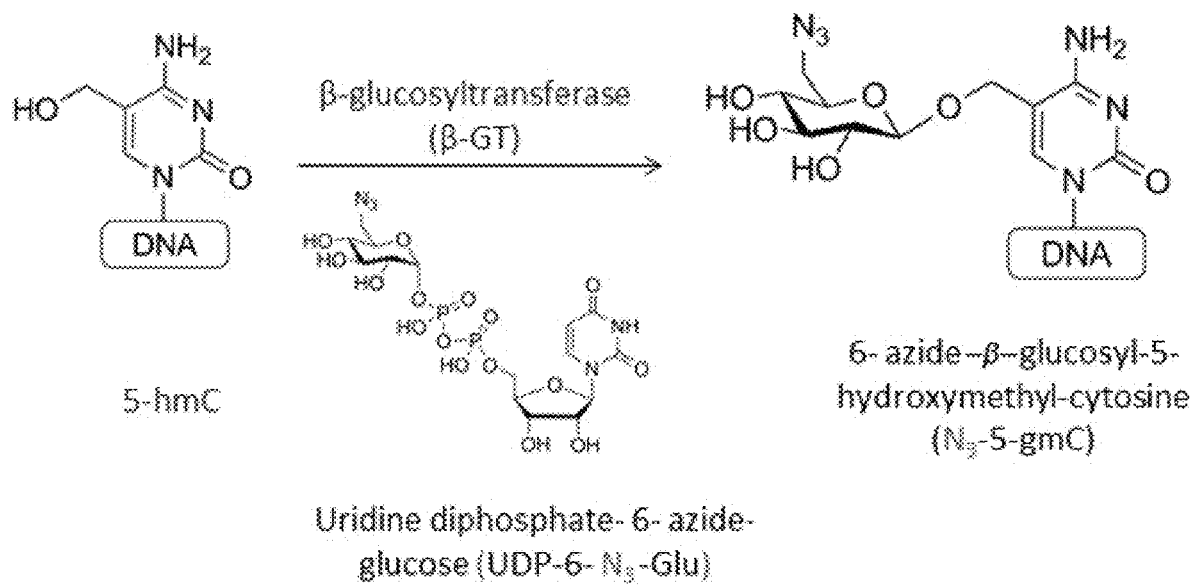
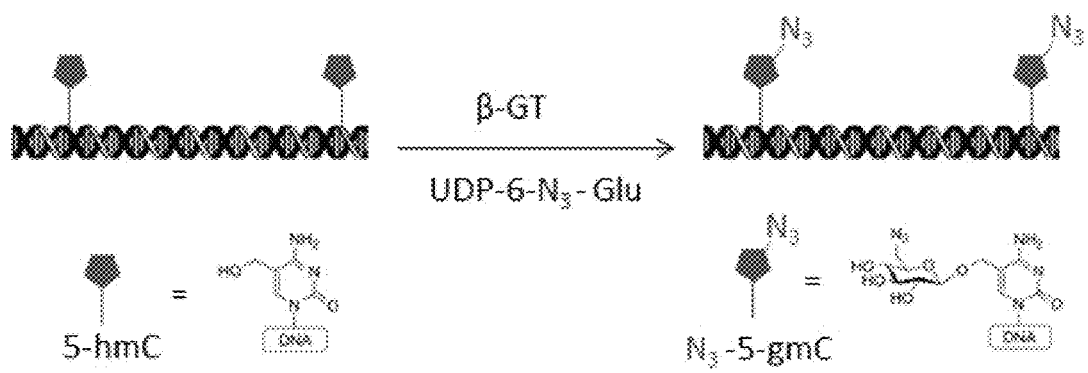
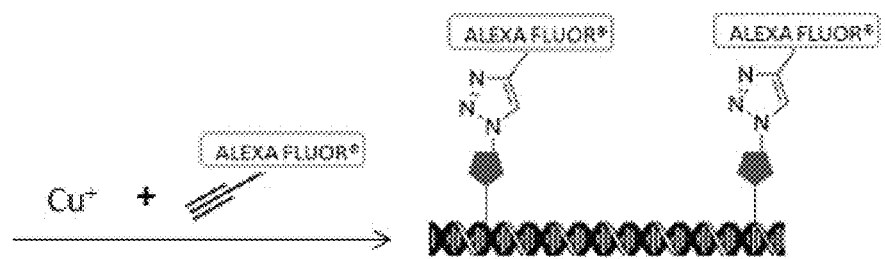
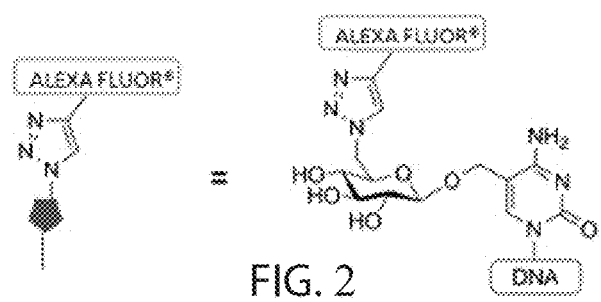
FIG. 2

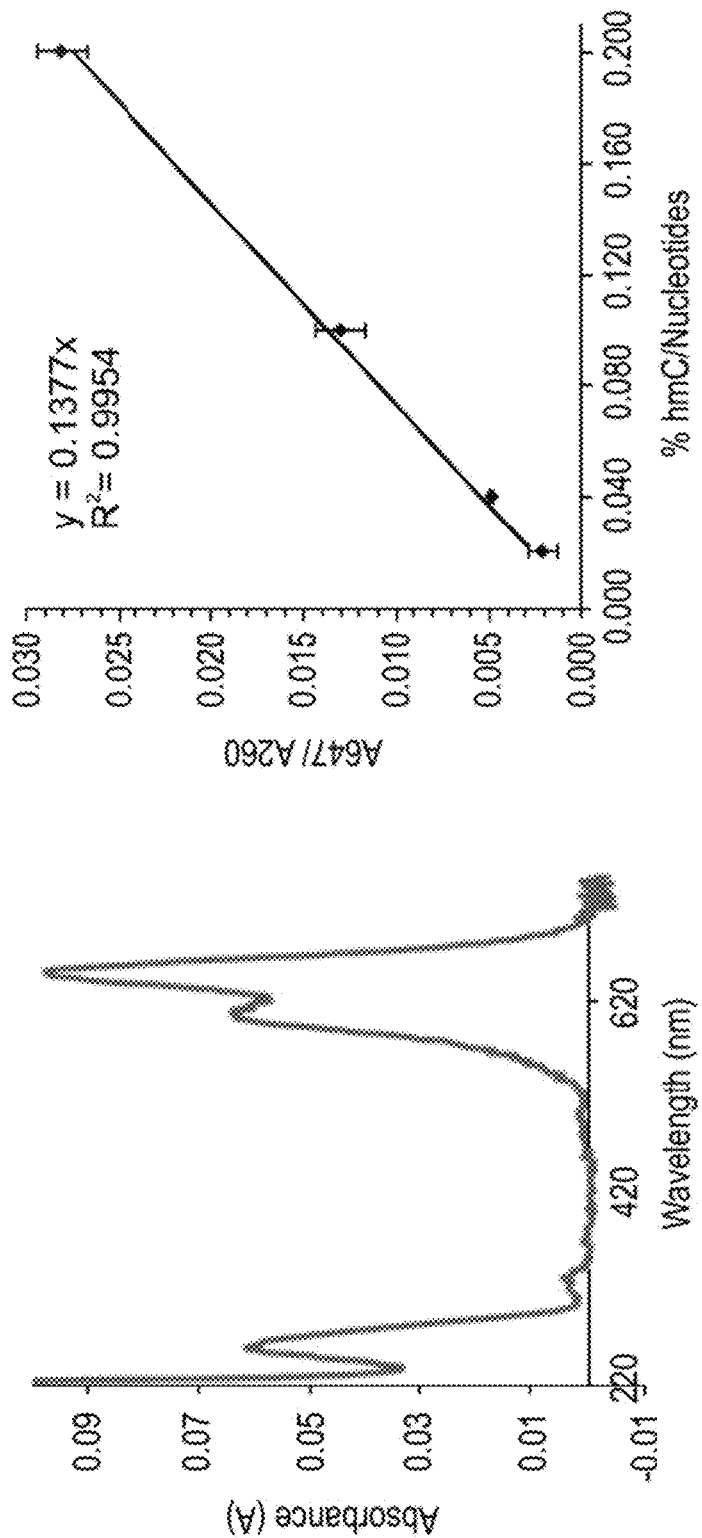

FIG. 6B

| Repetitions | Blank | Brain | Small brain | Kidney | Lung | Liver |
|---|---|---|---|---|---|---|
| 1 | 4 | 519 | 984 | 178 | 177 | 33 |
| 2 | 4 | 518 | 967 | 172 | 172 | 30 |

| %hmC | Blank | 0.02 | 0.04 | 0.08 | 0.1 | 0.2 |
|---|---|---|---|---|---|---|
| Plasmid + hmC | 8 | 104 | 243 | 339 | 434 | 1301 |
| Plasmid + Cy5 | 0 | 177 | 522 | 962 | 1406 | 2786 |

SEQUENCE LISTING

```
<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: Single strand DNA oligonucleotide

<400> SEQUENCE: 1
ctcatgctga aaacgtggtg                                            20

<210> SEQ ID NO 2
<211> LENGTH: 20
<212> TYPE: DNA
<213> ORGANISM: Artificial Sequence
<220> FEATURE:
<223> OTHER INFORMATION: Single strand DNA oligonucleotide

<400> SEQUENCE: 2
ggacaggacc agcatacgat                                            20

<210> SEQ ID NO 3
```

-continued

```
<211> LENGTH: 20
<212> TYPE: DNA
<213> ORGANISM: Artificial Sequence
<220> FEATURE:
<223> OTHER INFORMATION: Single strand DNA oligonucleotide
<220> FEATURE:
<221> NAME/KEY: modified_base
<222> LOCATION: (1)..(1)
<223> OTHER INFORMATION: 5' Alexa Fluor; 488 (NHS Ester) conugated
      nucleotide

<400> SEQUENCE: 3
taaattagtt acacaggaaa                                              20

<210> SEQ ID NO 4
<211> LENGTH: 19
<212> TYPE: DNA
<213> ORGANISM: Artificial Sequence
<220> FEATURE:
<223> OTHER INFORMATION: Single strand DNA oligonucleotide

<400> SEQUENCE: 4
aagccacaac tctaatttt                                               19

<210> SEQ ID NO 5
<211> LENGTH: 7
<212> TYPE: DNA
<213> ORGANISM: Artificial Sequence
<220> FEATURE:
<223> OTHER INFORMATION: Restriction site of endonuclease BspQI

<400> SEQUENCE: 5 gctcttc                                                             7
```

DETECTION OF HYDROXYMETHYLCYTOSINE BASES

RELATED APPLICATIONS

This application is a continuation of U.S. patent application Ser. No. 16/424,523, filed on May 29, 2019 and matured to U.S. Pat. No. 11,091,793, which is a division of U.S. patent application Ser. No. 14/894,350 filed on Nov. 26, 2015, now U.S. Pat. No. 10,351,898, which is National Phase of PCT Patent Application No. PCT/IL2014/050010 having International Filing Date of Jan. 5, 2014, which claims the benefit of priority under 35 USC § 119(e) of U.S. Provisional Patent Application No. 61/828,129 filed on May 28, 2013. The contents of the above applications are all incorporated by reference as if fully set forth herein in their entirety.

SEQUENCE LISTING STATEMENT

The ASCII file, entitled 88954SequenceListing.txt, created on Aug. 12, 2021, comprising 1,431 bytes, submitted concurrently with the filing of this application is incorporated herein by reference.

FIELD AND BACKGROUND OF THE INVENTION

The present invention, in some embodiments thereof, relates to molecular biology and, more particularly, but not exclusively, to detection and mapping of 5-hydroxymethyl cytosine bases within single or plurality of DNA molecules.

Epigenetics refers to DNA and chromatic modifications that persist from one cell division to the next without change in the underlying DNA sequence. These dynamic, chemical modifications are a major source of genomic variation, yet this variation is difficult to detect by current technologies since it is masked by ensemble averaging.

Epigenetic modifications include cytosine methylation (5mC) and the recently discovered cytosine hydroxymethylation (5hmC), which exhibits tissue and cell type specific distribution in mammalian genomes.

In recent studies of genomic DNA from human and mouse brain tissue and mouse embryonic stem cells, it was found that a substantial fraction of 5-methyl-cytosine (5mC) in CpG dinucleotides is converted to 5hmC by the action of the Tet family Fe(II)-dependent oxygenases. The distribution of 5hmC in mammals is tissue specific and non-random, suggesting that its deposition is highly regulated and that it may have a functional role in transcription regulation. Today, 5hmC is widely accepted as the sixth base of DNA (after 5-methylcytosine, the fifth base), and it is in the focus of extensive research.

To elucidate the role of 5hmC, information regarding quantity and distribution is critical, and several methods for the specific detection of 5hmC have been reported since its discovery in mammalian tissue in 2009 [M. Münzel, D. Globisch, and T. Carell, *Angewandte Chemie (International ed. in English)*, 2011, 50, 6460-8].

Selective functionalization of 5hmC is based on the discovery that T4 β-glucosyltransferase (β-GT) from T-4 bacteriophages can attach a glucose moiety from uridine diphosphoglucose (UDP-Glu) onto the hydroxyl group of 5hmC, resulting in a glucosylated nucleotide. Song et al. [in *Nature biotechnology*, 2011, 29, 68-72 and U.S. patent application having Publication No. 2011/0301045] utilized this enzymatic process to transfer a glucose chemically modified with an azide group onto 5hmC in genomic DNA. Using Huisgen cycloaddition (click) chemistry, they attached a biotin to the azide group and captured the 5hmC-containing DNA on streptavidin-coated magnetic beads for sequencing. A commercially available product, the Hydroxymethyl Collector™ (by Active Motif), for detecting and capturing DNA fragments containing 5-hmC methylation, was developed based on this methodology.

However, due to the short sequence reads, sequencing reports on the population averaged distribution of 5hmC cannot resolve small sub-populations or characterize variation in the 5hmC patterns, which are required for identifying epigenetic modifications which may display high cell to cell variation due to their dynamic nature.

SUMMARY OF THE INVENTION

According to an aspect of some embodiments of the present invention there is provided a method of labeling the epigenetic modification 5-hydroxymethyl-cytosine (5hmC) along a DNA molecule:

(a) attaching to the DNA molecule a 5hmc specific labeling agent; and (b) extending the DNA molecule.

According to some embodiments of the invention, the extending is linearly extending.

According to some embodiments of the invention, step (b) is effected following step (a).

According to some embodiments of the invention, the method further comprises attaching to the DNA molecule an additional labeling agent distinct of the 5hmc specific labeling agent.

According to some embodiments of the invention, the additional labeling agent is a 5mc specific labeling agent.

According to some embodiments of the invention, the additional labeling agent is an epigenetic modification specific labeling agent.

According to some embodiments of the invention, the additional labeling agent is a non-epigenetic modification specific labeling agent.

According to some embodiments of the invention, the does not comprise subjecting the DNA molecule to fragmentation.

According to some embodiments of the invention, the extending is effected by depositing the DNA molecule on a surface or extending the DNA molecule in a nanochannel.

According to some embodiments of the invention, the method further comprises identifying a position of the 5-hydroxymethyl-cytosine (5hmC) along the DNA molecule.

According to some embodiments of the invention, attaching the labeling agent comprises:

reacting a labeling agent derivatized by a second reactive group with a DNA molecule in which the 5-hydroxymethylcytosines are glycosylated by a glucose molecule derivatized by a first reactive group, wherein the first and second reactive groups are chemically compatible to one another.

According to some embodiments of the invention, glycosylating the 5-hydroxymethylcytosines in the DNA molecule comprises incubating the DNA molecule with β-glucosyltransferase and a uridine diphosphoglucose (UDP-Glu) derivatized by the first reactive group.

According to some embodiments of the invention, one of the first and second reactive groups is azide and the other is alkyne, such that attaching the labeling agent to the DNA molecule is effected by a click chemistry.

According to some embodiments of the invention, the reacting is free of a copper catalyst.

According to some embodiments of the invention, the first reactive group is azide.

According to some embodiments of the invention, the uridine diphosphoglucose (UDP-Glu) derivatized by the first reactive group is a UDP-6-$N_3$-Glucose. According to some embodiments of the invention, the UDP-6-$N_3$-Glucose is synthesized chemically.

According to some embodiments of the invention, the UDP-6-$N_3$-Glucose is synthesized enzymatically.

According to some embodiments of the invention, the labeling agent is a fluorescent labeling agent.

According to an aspect of some embodiments of the present invention there is provided a method of in-situ imaging a DNA molecule, the method comprising:

(a) attaching a labeling agent to the DNA molecule according to the method of any one of claims 11-15; and (b) subjecting the DNA molecule to an imaging method suitable for detecting the labeling agent.

According to some embodiments of the invention, the labeling agent is a fluorescent agent and the imaging method is a fluorescence imaging.

According to some embodiments of the invention, the method further comprises generating an optical image of the DNA molecule following the imaging.

According to an aspect of some embodiments of the present invention there is provided an extended DNA molecule comprising at least one 5hmc-specific labeling agent.

According to an aspect of some embodiments of the present invention there is provided a DNA molecule comprising at least two different labeling agents, wherein a first labeling agent of the at least two different labels is a 5hmc-specific labeling agent.

According to some embodiments of the invention, the 5hmc-specific labeling agent is attached to the DNA molecule by reacting a labeling agent derivatized by a second reactive group with a DNA molecule in which the 5-hydroxymethylcytosines are glycosylated by a glucose molecule derivatized by a first reactive group, wherein the first and second reactive groups are chemically compatible to one another.

According to some embodiments of the invention, one the first and second reactive groups is azide and the other is alkyne, such that attaching the labeling agent to the DNA molecule is effected by a click chemistry.

According to some embodiments of the invention, the reacting is free of a copper catalyst.

According to some embodiments of the invention, the first reactive group is azide.

According to some embodiments of the invention, the labeling agent is a fluorescent labeling agent.

According to some embodiments of the invention, a second labeling agent of the at least two different labeling agents is a 5mc-specific labeling agent.

According to some embodiments of the invention, a second labeling agent of the at least two different labeling agents is for an epigenetic modification.

According to some embodiments of the invention, a second labeling agent of the at least two different labeling agents is for a non-epigenetically modified base.

According to some embodiments of the invention, the DNA molecule is extended.

According to some embodiments of the invention, the DNA molecule is a genomic DNA molecule.

According to some embodiments of the invention, the DNA molecule is longer than 20 Kb.

According to some embodiments of the invention, the DNA molecule is longer than 30 Kb.

According to some embodiments of the invention, the DNA molecule is longer than 40 Kb.

According to an aspect of some embodiments of the present invention there is provided a method of detecting 5-hydroxymethyl-cytosine (5hmC) in a DNA sample the method comprising:

(a) reacting the DNA sample with a 5hmc-specific fluorescent agent under conditions which allow staining of the DNA sample with the 5hmc-specific labeling agent so as to obtain a 5hmC-labeled DNA sample; and (b) measuring fluorescence intensity of the 5hmC-labeled DNA sample (X) and absorption intensity of the DNA, at 260 nm (Y), wherein a ratio between X to Y is indicative of presence or level of 5hmC in the DNA sample.

According to some embodiments of the invention, the ratio is compared to a ratiometric calibration curve.

According to some embodiments of the invention, the detecting is effected in a high throughput setting of at least 300 DNA samples.

According to an aspect of some embodiments of the present invention there is provided a composition-of-matter comprising the DNA molecule, as described herein.

According to some embodiments of the invention, the DNA molecule is surface deposited or extended in a microchannel.

According to an aspect of some embodiments of the present invention there is provided a method of preparing UDP-6-$N_3$-Glucose, the method comprising subjecting an azido glucose (6-azido glucose) to an enzymatic catalysis by kinase N-acetylhexoseamine 1-kinase (NahK), in the presence of ATP to thereby obtain a phosphorylated 6-azidoglucose; and subjecting the phosphorylated 6-azido glucose to enzymatic catalysis by uridyltransferase (GlmU) in the presence of UTP.

According to an aspect of some embodiments of the present invention there is provided a computer readable storage medium comprising a database including a plurality of DNA sequences and information pertaining to 5hmC modification of the plurality of DNA sequences.

According to some embodiments of the invention, wherein the information is selected from the group consisting of, position of the 5hmC, level of the 5hmC, tissue distribution of the 5hmC.

In view of the limitations in detecting small sub-populations of 5hmC modifications and/or in characterizing variation in the 5hmC patterns, which are associated with variations in the distribution of 5hmC, a need for a single-molecule detection of 5hmC-modified DNA has been recognized.

The present inventors have designed and successfully practiced a methodology for specific labelling of the epigenetic modification 5-hydroxymethyl-cytosine along genomic DNA molecules with a labeling agent such as a fluorescent reporter molecule. The disclosed methodology is based on enzymatic glucosylation followed by a click chemistry reaction, and enables single molecule detection as well as global quantification of 5hmC in genomic DNA.

Embodiments of the invention relate to methods of labeling DNA and imaging the labeled DNA molecule at the single molecule level while maintaining high sensitivity. The ability to specifically label epigenetic information holds promise in single-molecule DNA barcoding applications. These methods bridge the gap between the single-base resolution but short reads of sequencing methods and the long range genomic context but low resolution (Mbp) of cytogenetic techniques such as chromosome fluorescence in situ hybridization (FISH). An emerging technology that utilizes DNA barcoding is optical mapping. This technique uses fluorescence imaging of linearly extended DNA molecules to probe information patterns along the molecules. Before imaging, DNA is deposited on surfaces or extended in nanochannels, and sequence-specific information, such as locations of enzymatic recognition sites, is readout along the DNA like beads on a string. This barcoding technique is focused on sequence-specific labeling that provides information regarding the genetic identity of the observed molecule. The detected pattern can be used as a scaffold for assembling and finishing sequencing data but also to detect structural variations. The ability to simultaneously record epigenetic information such as the DNA modifications 5mC and 5hmC as well as the distribution of histones and transcription factors, may reveal long-range epigenetic patterns along individual chromosomes and highlight genomic variation hidden or inaccessible by traditional techniques.

Using the methodology disclosed herein, a simple and quick UV-vis measurement replaces currently used radioactive, mass-spec and affinity based methods.

The methodology described herein can be used as a substitute to immunostaining in histological samples, tissue sections, chromosomes and other cytogenetic applications.

Single molecule optical patterns may serve as biomarkers for early diagnostics as well as for monitoring the bioactivity of drugs that influence hydroxymethylation.

Embodiments of the present invention further relate to a preparation of UDP-azide glucose, an exemplary reagent useful in the methodology described herein, for specifically labeling 5hmC in a DNA molecule, via simple enzymatic reactions.

The UDP-azide glucose can be used for introducing an azide (reactive) group to hydroxymethylcytosine to which various functional groups can be attached via click chemistry. Such functional groups include biotin or other affinity tags as well as various contrast agents such as radiolabeling agents and isotopic labeling agents.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 2 is a scheme showing 5hmC labeling by enzymatic glucosylation, followed by a click chemistry reaction to thereby attach selectively a labeling agent (e.g., ALEXA FLUOR®) to 5hmc, according to exemplary embodiments of the present invention.

Figure 3A:
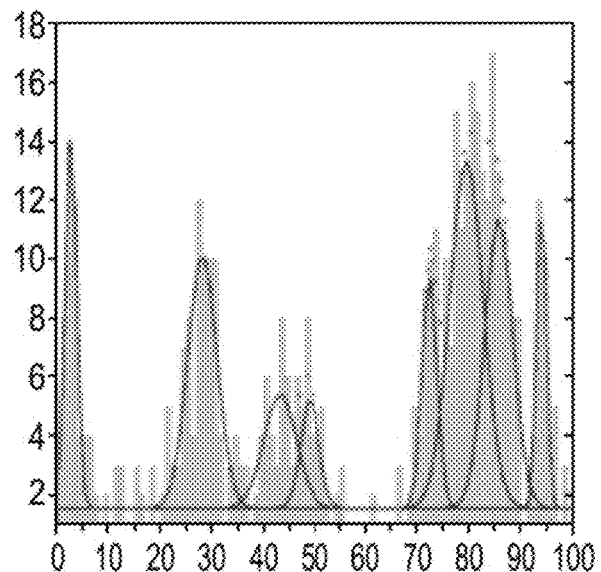
Figure 3C:
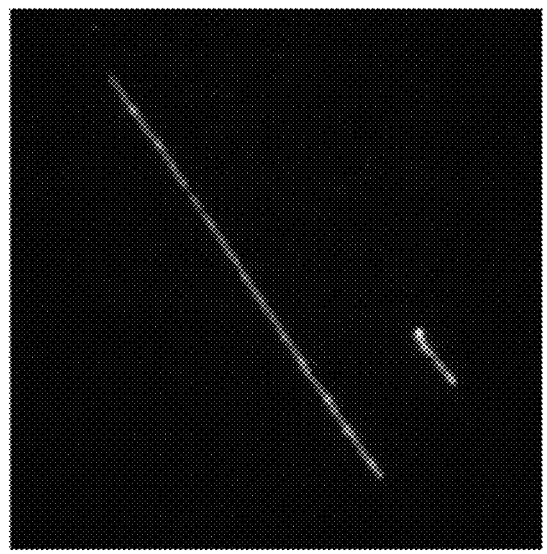
Figure 3B:
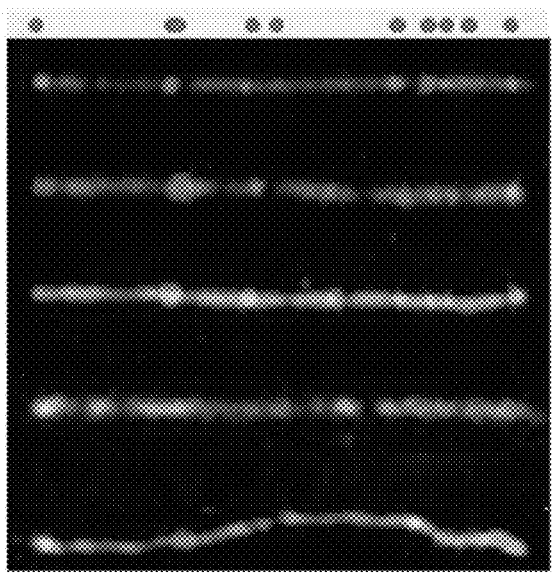
Figure 3D:
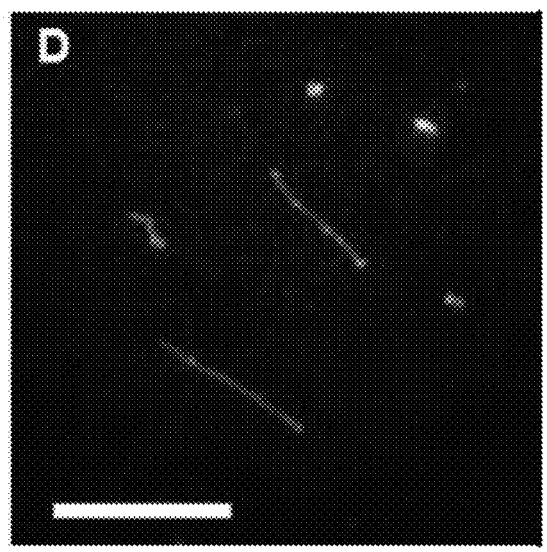

FIGS. 3A-3D are images showing single molecule detection of 5hmC. FIGS. 3A-3B: Mapping of 5hmC sites on lambda phage genomes. FIG. 3A is a histogram built from the 5hmC position maps of 93 genomes. A combination of eight Gaussians (red dashed line) centered on the expected 5hmC sites (black solid line) nicely represents the experimental data. FIG. 3B is a single-molecule image of lambda phage genomes (green) labeled with ALEXA FLUOR®) 555 (red). The optical patterns match the expected optical map (red dots, upper panel). FIGS. 3C-3D are single molecule images of DNA extracted from mouse tissues. DNA (green) was extracted from brain (FIG. 3C) and kidney (FIG. 3D) and 5hmC was labeled with Cy5 (red). (scale bar 10 μm/~35 Kbp).

FIGS. 4A-4B are graphs showing quantification of 5hmC levels in soluble DNA samples. FIG. 4A shows an absorbance spectrum of a PCR-amplified, 70-bp DNA molecule containing three 5hmC residues, labeled with ALEXA FLUOR®) 647. The absorption peaks at 260 nm and 650 nm correspond to the absorption maxima of DNA and of ALEXA FLUOR®) 647 respectively. FIG. 4B is a calibration curve of the ratio between the absorbance at 260 nm (nucleotide bases) and at 650 nm (5hmC-ALEXA FLUOR® 647 label) as a function of % 5hmC per total nucleotides. Each data point represents an average of three measurements.

Figure 5A:
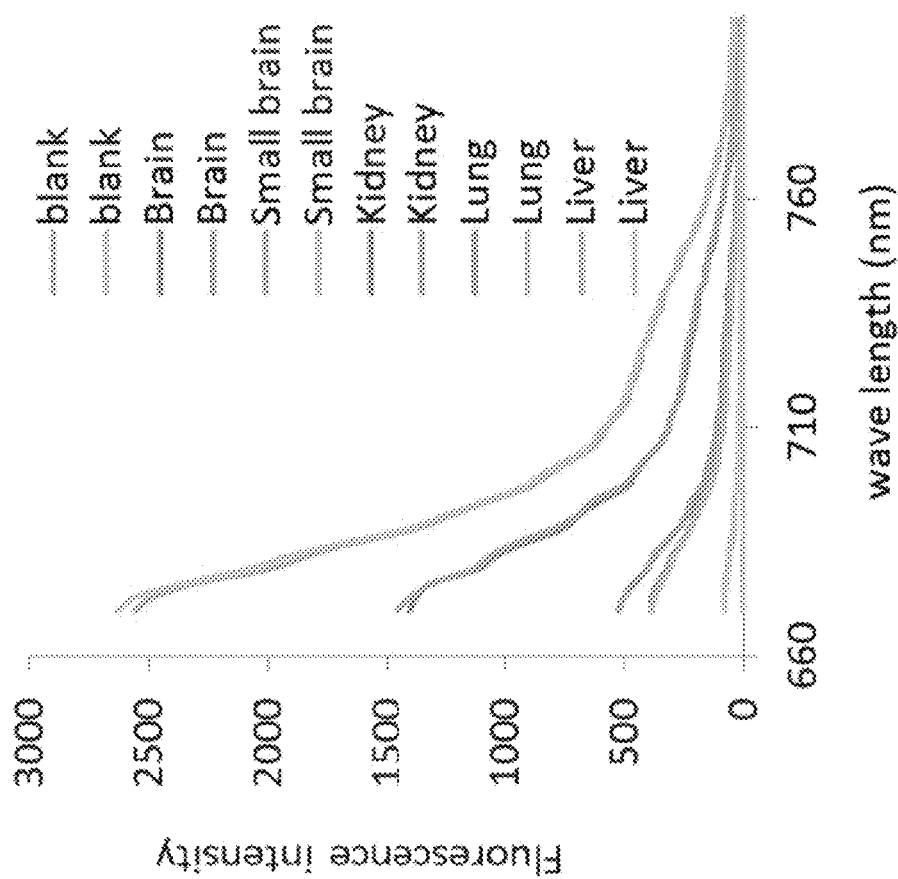
Figure 5B:
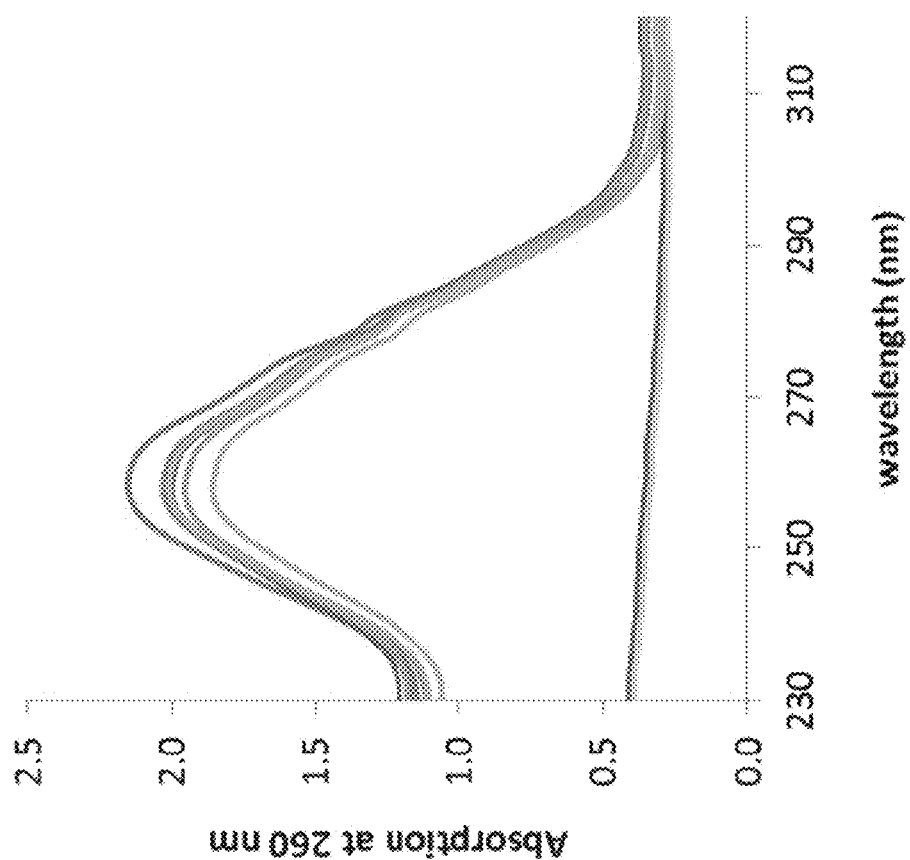

FIGS. 5A-5B are graphs showing absorption spectrum of DNA (FIG. 5A), and fluorescence emission spectrum (FIG. 5B) of hmC labeled with Cy5 by the click reaction from different tissues.

Figure 6A:
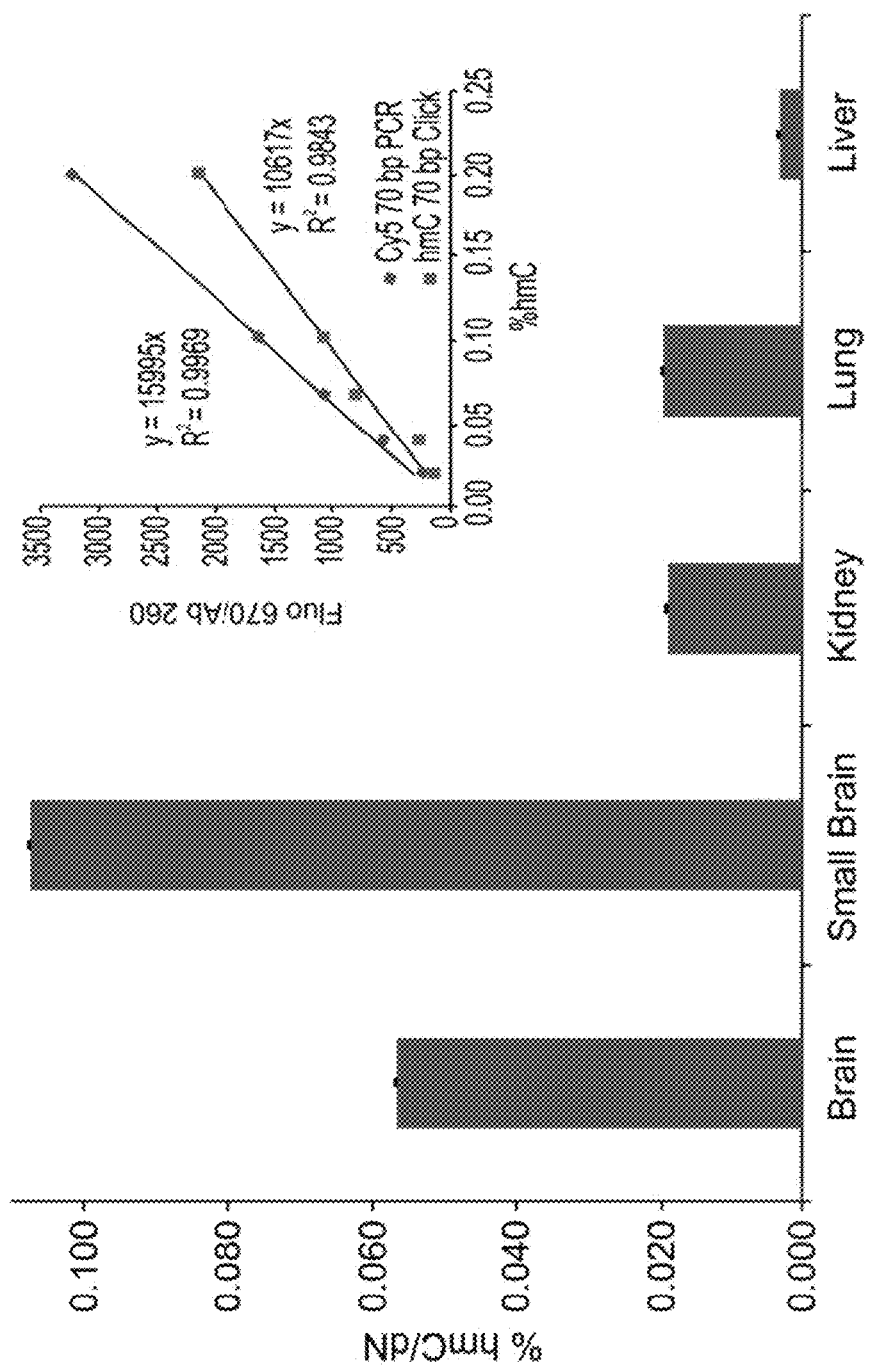

FIG. 6A is a graphic presentation showing the percent of hydroxymethylated cytosine out of total nucleotides in various tissues. Samples were scanned from a 384 well plate, by a plate reader. The % hmC was calculated from the ratio of the fluorescence at 670 nm and the absorption at 260 nm, which is compared to a calibration cure (insert) prepared with known % hmC. Red dots represents a calibration curve prepared from DNA with known percentage of hmC, labeled with Cy5 following the enzymatic and click reaction. The blue dots represent a calibration curve made of DNA fragments containing known percentage of Cy5. These fragments are made by PCR with Cy5-labeled cytosines, among the other nucleotides. The ratio between the slope of these two calibration curves indicate the efficiency of the hmC labeling reaction.

FIG. 6B is a heat map of the ratio F670/A260 for the given samples as it is scanned by the plate reader.

Figure 7A:
Figure 7B:
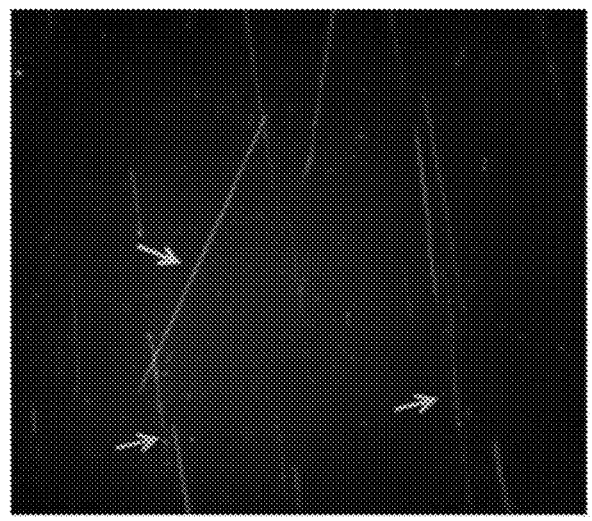
Figure 7C:
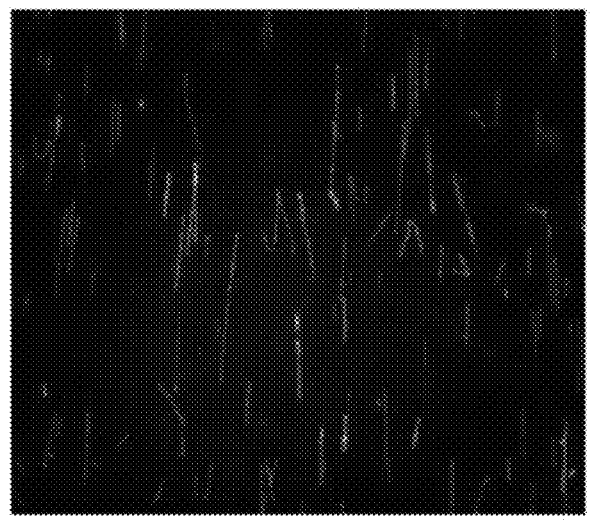

FIGS. 7A-7C are images showing single DNA fragments (green strings labeled with YoYo-1) stretched on modified glass slides and labeled for hmC with Cy5 (red dots). DNA was extracted from PBMC (FIG. 7A), spleen (FIG. 7B) and brain (FIG. 7C) tissues. Blue arrows point to fragments containing high hmC density and Orange arrows for fragments containing low hmC labels.

Figure 8B:
Figure 8A:
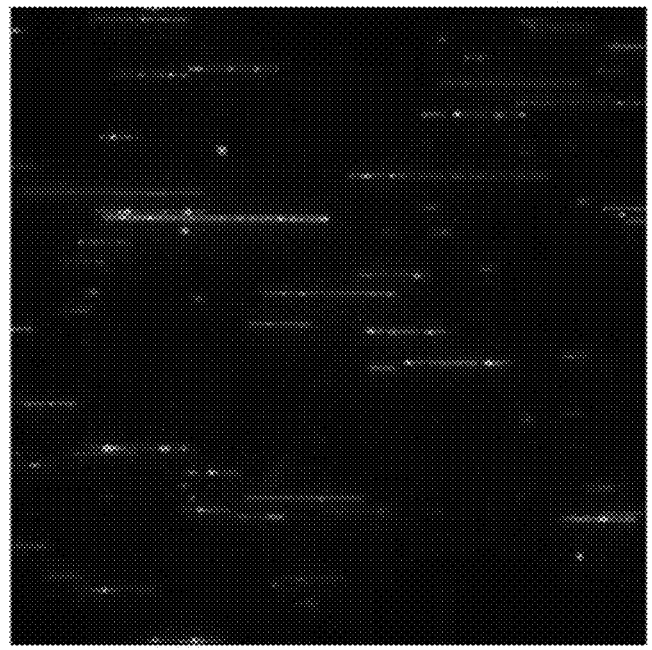

FIGS. 8A-8B are images showing DNA fragments stretched on a glass slide, extracted from Zebra fish (FIG. 8A) and from mouse brain (FIG. 8B), labeled with YoYo-1 (blue). Click chemistry was used for the labeling of hmC sites with Cy5 (pink) and the nicked regions, forming the DNA barcoding are labeled with Atto 550 (green).

DESCRIPTION OF SPECIFIC EMBODIMENTS OF THE INVENTION

The present invention, in some embodiments thereof, relates to molecular biology and, more particularly, but not exclusively, to detection and mapping of 5-hydroxymethyl cytosine bases within a DNA molecule.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The epigenetic modification 5-hydroxymethyl-cytosine is a DNA pyrimidine nitrogen base. A methyl group and then a hydroxy group are added to a cytosine base. It is important in epigenetics, because the hydroxymethyl group on the cytosine can possibly switch gene expression. To date the exact role of 5hmC is poorly understood. Thus, elucidating the role of 5hmC and gathering information regarding the quantity and distribution of this nucleotide is critical.

Whilst conceiving the present invention, and reducing it to practice, the present inventors have devised a specifically detectable agent for 5hmC which can be used to label 5hmC along genomic DNA molecules with a fluorescent reporter molecule. Enzymatic glucosylation followed by a click chemistry reaction enables single molecule detection as well as global quantification of 5hmC in genomic DNA.

As is illustrated hereinbelow and in the Examples section which follows, the present inventors have devised a novel method for labeling and detecting 5hmC sites with a fluorescent reporter molecule (labeling agent) in which DNA molecules can be imaged at the single molecule level and a plurality of DNA molecules can be analyzed in high throughput settings. An exemplary labeling scheme is provided in FIG. 2 and in Example 1 below. As shown, a glucosyltransferase is fed with a synthetic cofactor UDP-6-$N_3$-Glu, resulting in covalent attachment of a functional azide at the 5hmC site (FIG. 2).

This azide is further reacted with an ALEXA FLUOR® alkyne via a "click" chemistry reaction to generate the fluorescently labeled 5hmC (FIG. 2). The resulting DNA product has fluorescence and absorbance proportional to the content of 5hmC residues.

The present inventors have exploited the ability to specifically label epigenetic information in single-molecule DNA barcoding applications. These methods bridge the gap between the single-base resolution but short reads of sequencing methods and the long range genomic context but low resolution (Mbp) of cytogenetic techniques such as chromosome fluorescence in situ hybridization (FISH).

Thus, the present inventors have further used optical imaging in order to detect 5hmC at the individual molecule level. This technique employs fluorescence imaging of linearly extended DNA molecules to probe information patterns along the molecules. Before imaging, labeled DNA is deposited on surfaces or extended in nanochannels, and sequence-specific information, such as locations of 5hmC, enzymatic recognition sites, histones and the like is readout along the DNA like beads on a string (see Example 1). The use of fluorescent dyes that are sequence-specifically incorporated such as by an enzymatic reaction and that are imaged as fluorescent spots along the DNA result in barcoding techniques which provide information regarding the genetic identity of the observed molecule. The ability to simultaneously record epigenetic information such as the DNA modifications 5mC and 5hmC as well as the distribution of histones and transcription factors, may reveal long-range epigenetic patterns along individual chromosomes and highlight genomic variation hidden or inaccessible by traditional techniques.

Using the present teachings, the present inventors were able to detect a single label within a 50-kb genome corresponding to a 5hmC content of 0.002%, demonstrating unprecedented sensitivity.

While further reducing the present invention to practice, the present inventors have realized that calculating the fluorescence intensity (rather than the absorption) of a hmC-labeled DNA sample and the absorption intensity of the DNA, at 260 nm (FIGS. 5A-5B) provides very sensitive detection which is far higher than that detected by absorption measurements of labeled 5hmC, allowing to detect down to 0.004% hmC/dN from a DNA sample such as extracted from liver. This method negates the need for DNA immobilization thus rendering it technically accessible, cost effective and especially useful for determining 5hmC levels in high throughput settings.

In summary, a simple, fast, and cost-effective method is presented for the specific labeling of 5hmC with fluorescent reporter molecules. This method can be used to label engineered as well as native 5hmC sites on genomic DNA and demonstrate the potential of fluorescent labeling for single-molecule mapping of 5hmC patterns along genomic DNA. In addition, the labeling allows rapid screening and quantification of global 5hmC levels in genomic DNA using conventional UV-vis spectrophotometry with sensitivity that rivals currently existing methods for global 5hmC quantification.

Thus, according to an aspect of some embodiments of the present invention there is provided a method of labeling the epigenetic modification 5-hydroxymethyl-cytosine (5hmC) along a DNA molecule.

As used herein "5-Methylcytosine" or "5mC" is a methylated form of the DNA base cytosine. When cytosine is methylated, the DNA maintains the same sequence, but the expression of methylated genes can be altered (the study of this is part of the field of epigenetics). 5-Methylcytosine is incorporated in the nucleoside 5-methylcytidine.

As used herein "5-Hydroxymethylcytosine" or "5hmC" is a DNA pyrimidine nitrogen base. It is formed from the DNA base cytosine by adding a methyl group and then a hydroxy group.

As used herein the term "DNA" refers to single stranded DNA or a double stranded DNA which is isolated. The DNA can be a eukaryotic DNA (e.g., rodent or primate e.g., human) in which 5hmC modifications typically occur or a synthetic DNA in which 5hmC modifications may be artificially added.

According to an embodiment of the invention, the DNA molecule is a complementary polynucleotide sequence (cDNA) to which 5hmC modifications have been artificially added, a genomic polynucleotide sequence and/or a composite polynucleotide sequences (e.g., a combination of the above).

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exonal sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

The length of the DNA molecule may vary. Exemplary ranges include, but are not limited to 1-15,000 Kb, reflecting at the high range the size of a human chromosomes (or chromatin).

According to some embodiments of the invention, the DNA molecule is longer than 20 Kb.

According to some embodiments of the invention, the DNA molecule is longer than 30 Kb.

According to some embodiments of the invention, the DNA molecule is longer than 40 Kb.

Detection of the labeled DNA molecule can be done at the single molecule level (see FIGS. 3A-3D, 7A-7C and 8A-8B) using optical imaging as further described hereinbelow. Alternatively, detection of labeled DNA molecules can be done at the global level, analyzing the presence or level of 5hmC modification of a plurality of DNA molecules at the cell, tissue and organism level (as shown in FIGS. 5A-5B), as further described hereinbelow.

Thus, according to an embodiment of the invention there is provided a method of labeling the epigenetic modification 5-hydroxymethyl-cytosine (5hmC) along a (single) DNA molecule, the method comprising:

(a) attaching to the DNA molecule a 5hmc specific labeling agent; and (b) extending the DNA molecule.

As mentioned hereinabove and further described hereinbelow, attachment of a 5hmc specific labeling agent to the DNA molecule is effected when analysis is performed in the single molecule level or when a plurality of DNA molecules (global 5hmC analysis) are analyzed.

As used herein "a 5hmC specific labeling agent" refers to a labeling agent that differentiates between 5hmC modification and non-modified cytosine or methylated cytosine (5mC), as described hereinabove. A 5hmC specific labeling agent labels selectively the position or positions where 5hmC modification is present in a DNA molecule, and does not label those positions in a DNA molecule where 5mC or any other epigenetic modification is present. The 5hmC labeling agent according to some embodiments of the present invention is fluorescently detectable. A list of suitable labeling agents is provided hereinafter.

According to some embodiments of the invention, a 5hmC specific labeling agent labels at least 50%, or at least 70%, or at least 80%, or at least 90% of the a 5hmC modifications in a DNA molecule, including any intermediate within 50-100%.

According to some embodiments of the present invention, a 5hmC specific labeling agent is attached (e.g., covalently) selectively to 5hmC.

In some embodiments, selectively attaching a 5hmC specific labeling agent is effected by:

reacting a labeling agent derivatized by a reactive group (herein referred to as a second reactive group) with a DNA molecule in which the 5-hydroxymethylcytosine bases are glycosylated by a glucose molecule derivatized by another reactive group (herein referred to as a first reactive group).

The first and second reactive groups are selected as being chemical compatible to one another.

By "chemically compatible" it is meant that the first and second reactive groups can react with one another so as to form a chemical bond.

As used herein, the phrase "reactive group" describes a chemical group that is capable of undergoing a chemical reaction that typically leads to a bond formation. The bond can involve one or more of a covalent bond, an electrostatic bond, a hydrogen bond, aromatic interactions, and any combination thereof.

The bond, according to some embodiments of the present invention, is a covalent bond.

Chemical reactions that lead to a bond formation include, for example, cycloaddition reactions (such as the Diels-Alder's reaction, the 1,3-dipolar cycloaddition Huisgen reaction, and the similar "click reaction"), condensations, nucleophilic and electrophilic addition reactions, nucleophilic and electrophilic substitutions, addition and elimination reactions, alkylation reactions, rearrangement reactions and any other known organic reactions that involve a reactive group.

Representative examples of reactive groups include, without limitation, acyl halide, aldehyde, alkoxy, alkyne, amide, amine, aryloxy, azide, aziridine, azo, carbamate, carbonyl, carboxyl, carboxylate, cyano, diene, dienophile, epoxy, guanidine, guanyl, halide, hydrazide, hydrazine, hydroxy, hydroxylamine, imino, isocyanate, nitro, phosphate, phosphonate, sulfinyl, sulfonamide, sulfonate, thioalkoxy, thioaryloxy, thiocarbamate, thiocarbonyl, thiohydroxy, thiourea and urea, as these terms are defined hereinafter.

Exemplary first and second reactive groups that are chemically compatible with one another as described herein include, but are not limited to, hydroxy and carboxylic acid, which form an ester bond; thiol and carboxylic acid, which form a thioester bond; amine and carboxylic acid, which form an amide bond; aldehyde and amine, hydrazine, hydrazide, hydroxylamine, phenylhydrazine, semicarbazide or thiosemicarbazide, which form a Schiff base (imine bond); alkene and diene, which react therebetween via cycloaddition reactions; and reactive groups that can participate in a Click reaction.

Additional examples of pairs of reactive groups (first and second reactive groups) capable of reacting with one another include an azide and an alkyne, an unsaturated carbon-carbon bond (e.g., acrylate, methacrylate, maleimide) and a thiol, an unsaturated carbon-carbon bond and an amine, a carboxylic acid and an amine, a hydroxyl and an isocyanate, a carboxylic acid and an isocyanate, an amine and an isocyanate, a thiol and an isocyanate. Additional examples include an amine, a hydroxyl, a thiol or a carboxylic acid along with a nucleophilic leaving group (e.g., hydroxysuccinimide, a halogen).

It is to be appreciated that for each pair of reactive groups described hereinabove, either reactive group can correspond to the "first reactive group" or to the "second reactive group".

In some embodiments, the first and/or the second reactive groups can be latent groups, which are exposed during the chemical reaction, such that the reacting (e.g., covalent bond formation) is effected once a latent group is exposed. Exemplary such groups include, but are not limited to, reactive groups as described hereinabove, which are protected with a protecting group that is labile under selected reaction conditions.

Examples of labile protecting groups include, for example, carboxylate esters, which may hydrolyzed to form an alcohol and a carboxylic acid by exposure to acidic or basic conditions; silyl ethers such as trialkyl silyl ethers, which can be hydrolysed to an alcohol by acid or fluoride ion; p-methoxybenzyl ethers, which may be hydrolysed to an alcohol, for example, by oxidizing conditions or acidic conditions; t-butyloxycarbonyl and 9-fluorenylmethyloxycarbonyl, which may be hydrolysed to an amine by a exposure to basic conditions; sulfonamides, which may be hydrolysed to a sulfonate and amine by exposure to a suitable reagent such as samarium iodide or tributyltin hydride; acetals and ketals, which may be hydrolysed to form an aldehyde or ketone, respectively, along with an alcohol or diol, by exposure o acidic conditions; acylals (i.e., wherein a carbon atom is attached to two carboxylate groups), which may be hydrolysed to an aldehyde of ketone, for example, by exposure to a Lewis acid; orthoesters (i.e., wherein a carbon atom is attached to three alkoxy or aryloxy groups), which may be hydrolysed to a carboxylate ester (which may be further hydrolysed as described hereinabove) by exposure to mildly acidic conditions; 2-cyanoethyl phosphates, which may be converted to a phosphate by exposure to mildly basic conditions; methylphosphates, which may be hydrolysed to phosphates by exposure to strong nucleophiles; phosphates, which may be hydrolysed to alcohols, for example, by exposure to phosphatases; and aldehydes, which may be converted to carboxylic acids, for example, by exposure to an oxidizing agent.

According to some embodiments of the present invention, a linking moiety is formed as a result of a bond-forming reaction between two (first and second) reactive groups.

Exemplary linking moieties, according to some embodiments of the present invention, which are formed between a first and a second reactive groups as described herein include without limitation, amide, lactone, lactam, carboxylate (ester), cycloalkene (e.g., cyclohexene), heteroalicyclic, heteroaryl, triazine, triazole, disulfide, imine, aldimine, ketimine, hydrazone, semicarbazone and the likes. Other linking moieties are defined hereinbelow.

For example, a reaction between a diene reactive group and a dienophile reactive group, e.g. a Diels-Alder reaction, would form a cycloalkene linking moiety, and in most cases a cyclohexene linking moiety. In another example, an amine reactive group would form an amide linking moiety when reacted with a carboxyl reactive group. In another example, a hydroxyl reactive group would form an ester linking moiety when reacted with a carboxyl reactive group. In another example, a sulfhydryl reactive group would form a disulfide (—S—S—) linking moiety when reacted with another sulfhydryl reactive group under oxidation conditions, or a thioether (thioalkoxy) linking moiety when reacted with a halo reactive group or another leaving-reactive group. In another example, an alkynyl reactive group would form a triazole linking moiety by "click reaction" when reacted with an azide reactive group.

The "click reaction", also known as "click chemistry" is a name often used to describe a stepwise variant of the Huisgen 1,3-dipolar cycloaddition of azides and alkynes to yield 1,2,3-triazole. This reaction is carried out under ambient conditions, or under mild microwave irradiation, typically in the presence of a Cu(I) catalyst, and with exclusive regioselectivity for the 1,4-disubstituted triazole product when mediated by catalytic amounts of Cu(I) salts [V. Rostovtsev, L. G. Green, V. V. Fokin, K. B. Sharpless, *Angew. Chem. Int. Ed.* 2002, 41, 2596; H. C. Kolb, M. Finn, K. B. Sharpless, *Angew Chem., Int. Ed.* 2001, 40, 2004].

As demonstrated in the Examples section that follows, the "click reaction" is particularly suitable in the context of embodiments of the present invention since it can be carried out under conditions which are non-distructive to DNA molecules, and it affords attachment of a lebeling agent to 5hmC in a DNA molecule at high chemical yields using mild conditions in aqueous media. The selectivity of this reaction allows to perform the reaction with minimized or nullified use of protecting groups, which use often results in multistep cumbersome synthetic processes.

In exemplary embodiments, the first and second reactive groups comprise (in no particular order) an azide and an alkyne. These two reactive groups may combine to form a triazole ring, as defined herein, as a linking moiety. These two reactive groups thus combine to attach a labeling agent to the 5hmC in the DNA molecule by a mechanism referred to as "click" chemistry, as defined herein.

The term "derivatized", as used herein in the context of a labeling agent and a glucose, means that the labeling agent and/or the glucose are substituted, or are modified by substituting a position thereof, by a chemical moiety that comprises the respective (first or second) reactive group.

For example, a labeling agent derivatized by a second reactive group, as described herein, means that a labeling agent as described herein is modified so as to comprise a second reactive group as described herein, by substituting a position thereof with a chemical moiety that comprises the second reactive group. Alternatively, the second reactive group or a chemical moiety comprising the second reactive group already forms a part in a labeling agent as a substituent.

A chemical moiety that comprises the second reactive group can be the second reactive group per se or, for example, a spacer moiety that includes, and preferably terminates with, the second reactive group.

As used herein, the phrase "spacer moiety" describes a chemical moiety that typically extends between two chemical moieties and is attached to each of the chemical moieties via covalent bonds. The spacer moiety may be linear or cyclic, be branched or unbranched, rigid or flexible.

According to some embodiments of the present invention, the spacer moieties are selected such that they allow and/or promote the one or both of attachment of a second reactive group to the labeling agent and attachment of the labeling agent to the 5hmC in a DNA molecule. Such traits can be selected for in terms of spacer's length, flexibility, structure and specific chemical reactivity or lack thereof.

Exemplary spacer moieties include, but are not limited to, alkyl, alkenyl, alkynyl, cycloalkyl, heteroalicyclic, aryl, heteroaryl and/or a hydrocarbon chain having 1-20 carbon atoms and ending or interrupted by at least one heteroatom selected from the group consisting of O, S and N and/or containing from 0 to 19 unsaturated carbon-carbon or carbon-heteroatom bonds.

Additional spacer moieties include, without limitation, —$CH_2$—, —$CH_2$—O—, —$(CH_2)_2$—, —$(CH_2)_2$—O—, —$(CH_2)_3$—, —$(CH_2)_3$—O—, —$(CH_2)_4$—, —$(CH_2)_5$—, —$(CH_2)_6$—, —$(CH(CH_3))$—$CH_2$—, —CH=CH—CH=CH—, —C≡C—C≡C—, —$CH_2CH(OH)CH_2$—, —$CH_2$—O—$CH_2$—, —$CH_2$—O—$CH_2$—O—, —$(CH_2)_2$—O—$(CH_2)_2$—, —$(CH_2)_2$—O—$(CH_2)_2$—O—, —$CH_2$-m$C_6H_4$—$CH_2$—, —$CH_2$-m$C_6H_4$—$CH_2$—O—, —$CH_2$-p$C_6H_4$—$CH_2$—, —$CH_2$-p$C_6H_4$—$CH_2$—O—, —$CH_2$—NHCO—, —$C_6H_4$—NHCO—, —$CH_2$—O—

CH$_2$— and —CH═CH—CH$_2$—NH—(CH$_2$)$_2$—, and any combination thereof. Short polymeric chains, such as, for example, polyalkyelene glycols, are also contemplated.

In exemplary embodiments, a second reactive group as described herein is attached to a labeling agent via a spacer moiety, while exploiting functional groups present in the labeling agent for attaching thereto the spacer moiety which terminates with the second reactive group.

A labeling agent derivatized by a second reactive group as described herein can be selected and prepared using conventional chemical reactions, or can be a commercially available derivatized labeling agent.

In exemplary embodiments, the second reactive group is an alkyne and the labeling agent is derivatized by a chemical moiety that comprises an alkyne, as described herein. Such a chemical moiety can comprise, for example, dibezylcyclooctyne (DIBO), and can be attached to the labeling agent via a spacer as described herein.

According to some of these embodiments, the second reactive group is a "strained alkyne".

A "strained alkyne" is a cycloalkyne, preferably substituted by one or more groups that render it highly strained, for example, cyclopropyls, benzyls, and others. Examples of known strained alkynes include, but are not limited to, the following:

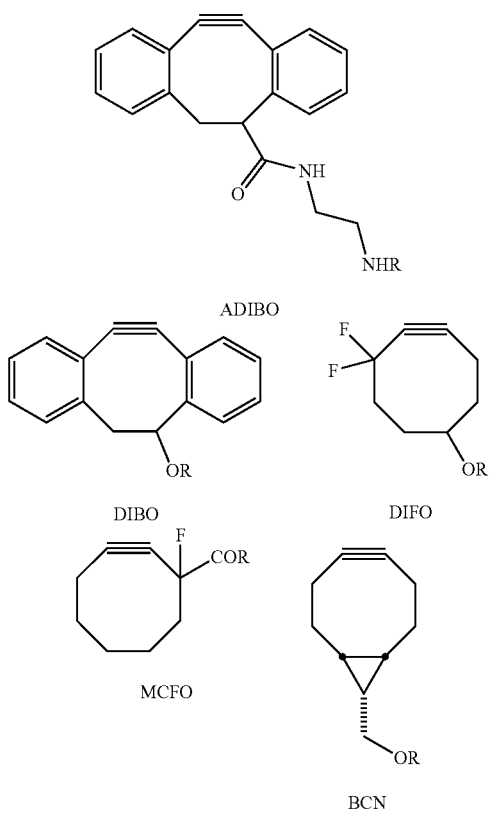

The use of a strained alkyl allows performing the click reaction without using a copper catalyst.

A glucose derivatized by a first reactive group describes a glucose moiety that is substituted at one position thereof by a chemical moiety that comprises the first reactive group, as described herein.

For example, one of the hydroxy groups of a glucose can be substituted by a chemical moiety that comprises the first reactive group or can be used to attach to the glucose the chemical moiety that comprises the first reactive group, via chemical reactions that involve a hydroxy group, as described herein.

A chemical moiety that comprises the first reactive group can be the first reactive group per se or, for example, a spacer moiety, as described herein, that includes, or terminates with, the first reactive group.

In exemplary embodiments, one of the hydroxy groups of a glucose is substituted (replaced) by a chemical moiety that comprises the first reactive group. Chemical reactions for substituting a hydroxy group are well known in the art.

In some of these embodiments, the first reactive group is azide and a hydroxy at position 6 of the glucose is substituted by an azide group.

Figure 1:
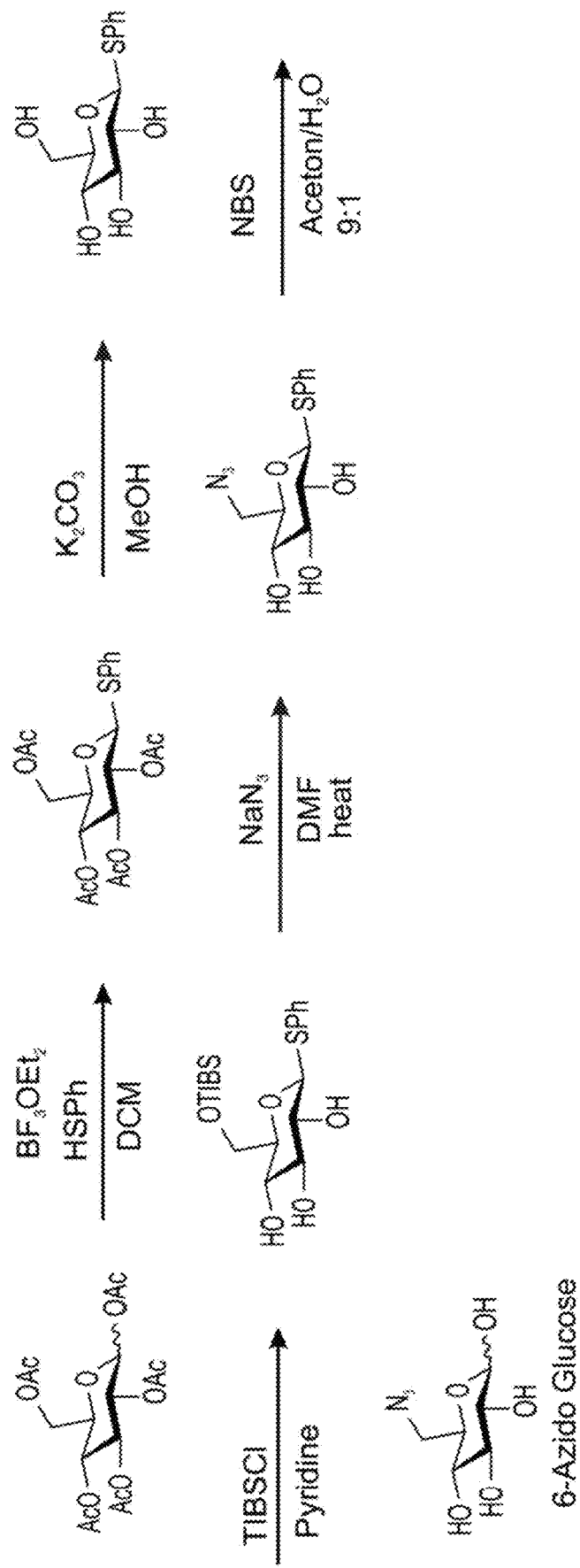
FIG. 1 is a scheme showing an exemplary synthesis of a 6-azido glucose, according to some embodiments of the present invention.

An exemplary synthetic pathway for preparing 6-azido-glucose is depicted in FIG. 1.

According to some embodiments of the invention, a DNA molecule in which the 5-hydroxymethylcytosine bases are glycosylated by a glucose molecule derivatized by the first reactive group is prepared, while utilizing a glucose derivatized by the first reactive group, as described herein.

In some embodiments, a selective introduction of a glucose derivatized by the first reactive group to 5-hydroxymethylcytosines in a DNA molecule comprises incubating the DNA molecule with β-glucosyltransferase and a uridine diphosphoglucose (UDP-Glu) derivatized by the first reactive group.

A DNA beta-glucosyltransferase (EC 2.4.1.27) is an enzyme that catalyzes the chemical reaction in which a beta-D-glucosyl residue is transferred from UDP-glucose to an hydroxymethylcytosine residue in DNA. This enzyme belongs to the family of glycosyltransferases, specifically the hexosyltransferases. The systematic name of this enzyme class is UDP-glucose:DNA beta-D-glucosyltransferase. Other names in common use include T4-HMC-beta-glucosyl transferase, T4-beta-glucosyl transferase, T4 phage beta-glucosyltransferase, UDP glucose-DNA beta-glucosyltransferase, and uridine diphosphoglucose-deoxyribonucleate beta-glucosyltransferase. In certain aspects, the a β-glucosyltransferase is a His-tag fusion protein.

In other embodiments, the protein may be used without the His-tag (hexa-histidine tag shown above) portion.

A uridine diphosphoglucose (UDP-Glu) derivatized by the first reactive group is meant to describe a uridine diphosphoglucose in which the glucose moiety is derivatized by a first reactive group, according to any one of the embodiments described herein.

In some embodiments, the uridine diphosphoglucose (UDP-Glu) derivatized by the first reactive group is a UDP-6-N$_3$-Glucose (see, FIG. 2).

A UDP-6-N$_3$-Glucose, or any other uridine diphosphoglucose (UDP-Glu) derivatized by the first reactive group, can be prepared by chemical synthesis, while utilizing, for example, a 6-azido glucose or any other derivatized glucose, or can be a commercially available product.

In some embodiments, the UDP-6-N$_3$-Glucose, or any other uridine diphosphoglucose (UDP-Glu) derivatized by the first reactive group, is prepared by enzymatically-catalyzed reactions, as exemplified in further detail hereinafter.

Once a glucose derivatized by a first reactive group is introduced to 5-hmCs in a DNA molecule, the DNA molecule is reacted with a labeling agent derivatized by a compatible second reactive group, as described herein.

As discussed hereinabove, in some embodiments, the reaction involves a click chemistry reaction.

According to some embodiments of the invention, the click chemistry reaction is free of a copper catalyst, namely, is effected without the presence of a copper catalyst or any other catalyst that may adversely affect the DNA molecule.

For any one of the embodiments described herein throughout, the phrase "labeling agent" refers to a detectable moiety or a probe. Exemplary labeling agents which are suitable for use in the context of these embodiments include, but are not limited to, a fluorescent agent, a radioactive agent, a magnetic agent, a chromophore, a bioluminescent agent, a chemiluminescent agent, a phosphorescent agent and a heavy metal cluster, as well as any other known detectable agents.

In some embodiments, the labeling agent is an agent that is detectable by spectrophotometric measurements, and/or which can be utilized to produce optical imaging. Such agents include, for example, chromophores, fluorescent agents, phosphorescent agents, and heavy metal clusters.

As used herein, the term "chromophore" refers to a chemical moiety that, when attached to another molecule, renders the latter colored and thus visible when various spectrophotometric measurements are applied.

The phrase "fluorescent agent" refers to a compound that emits light at a specific wavelength during exposure to radiation from an external source.

The phrase "phosphorescent agent" refers to a compound emitting light without appreciable heat or external excitation as by slow oxidation of phosphorous.

A heavy metal cluster can be for example a cluster of gold atoms used, for example, for labeling in electron microscopy techniques (e.g., AFM).

The term "bioluminescent agent" describes a substance which emits light by a biochemical process.

The term "chemiluminescent agent" describes a substance which emits light as the result of a chemical reaction.

According to some embodiments of the invention, the labeling agent is a fluorescent labeling agent.

A fluorescent agent can be a protein, quantum dots or small molecules. Common dye families include, but are not limited to Xanthene derivatives: fluorescein, rhodamine, Oregon green, eosin, Texas red etc.; Cyanine derivatives: cyanine, indocarbocyanine, oxacarbocyanine, thiacarbocyanine and merocyanine; Naphthalene derivatives (dansyl and prodan derivatives); Coumarin derivatives; oxadiazole derivatives: pyridyloxazole, nitrobenzoxadiazole and benzoxadiazole; Pyrene derivatives: Cascade Blue™ etc.; BODIPY™ (Invitrogen); Oxazine derivatives: Nile red, Nile blue, cresyl violet, oxazine 170 etc.; Acridine derivatives: proflavin, acridine orange, acridine yellow etc.; Arylmethine derivatives: auramine, crystal violet, malachite green; CF® dyes (Biotium); ALEXA FLUOR® (Invitrogen); Atto and Tracy (Sigma Aldrich); FLUOPROBES® (Interchim); Tetrapyrrole derivatives: porphin, phtalocyanine, bilirubin; cascade yellow; azure B; acridine orange; (4',6-diamidino-2-phenylindole) (DAPI); Hoechst 33258; lucifer yellow; piroxicam; quinine and anthraqinone; squarylium; oligophenylenes; and the like.

Other fluorophores include: Hydroxycoumarin; Aminocoumarin; Methoxycoumarin; Cascade Blue™; Pacific Blue™; Pacific Orange™; Lucifer yellow™; NBD; R-Phycoerythrin (PE); PE-Cy™5 conjugates; PE-Cy™7 conjugates; Red 613; PerCP; TruRed; FLUORX™; Fluorescein; BODIPY®-FL; tetramethylrhodamine (TRITC); X-Rhodamine; Lissamine Rhodamine B; Texas Red;

Aliaphycocyanin; APC-Cy™7 conjugates.

ALEXA FLUOR® dyes (Molecular Probes) include: ALEXA FLUOR® 350, ALEXA FLUOR® 405, ALEXA FLUOR® 430, ALEXA FLUOR® 488, ALEXA FLUOR® 500, ALEXA FLUOR® 514, ALEXA FLUOR® 532, ALEXA FLUOR® 546, ALEXA FLUOR® 555, ALEXA FLUOR® 568, ALEXA FLUOR® 594, ALEXA FLUOR® 610, ALEXA FLUOR® 633, ALEXA FLUOR® 647, ALEXA FLUOR® 660, ALEXA FLUOR® 680, ALEXA FLUOR® 700, ALEXA FLUOR® 750, and ALEXA FLUOR® 790.

Cy™ Dyes (BIOSYNTH® Laboratories Limited) include Cyt, Cy3, Cy3B, Cy3.5, Cy5, Cy5.5 and Cy7.

Nucleic acid probes include Hoechst 33342, DAPI, Hoechst 33258, SYTOX Blue, ChromomycinA3, Mithramycin, YOYO™-1, Ethidium Bromide, Acridine Orange, SYTOX Green, TOTO™-1, TO-PRO™-1, TO-PRO™: Cyanine Monomer, Thiazole Orange, Propidium Iodide (PI), LDS 751, 7-AAD, SYTOX Orange, TOTO™-3, TO-PRO™-3, and DRAQ5.

Cell function probes include Indo-1, Fluo-3, DCFH, DHR, SNARF.

Fluorescent proteins include Y66H, Y66F, EBFP, EBFP2, Azurite, GFPuv, T-Sapphire, Cerulean, mCFP, ECFP, CyPet, Y66W, mKeima-Red, TagCFP, AmCyan1, mTFP1, S65A, Midoriishi Cyan, Wild Type GFP, S65C, TurboGFP, TagGFP, S65L, Emerald, S65T (Invitrogen), EGFP (Ciontech), Azami Green (MBL), ZsGreen1 (Clontech), TagYFP (Evrogen), EYFP (Clontech), Topaz, Venus, mCitrine, YPet, Turbo YFP, ZsYellow1 (Clontech), Kusabira Orange (MBL), mOrange, mKO, TurboRFP (Evrogen), tdTomato, TagRFP (Evrogen), DsRed (Clontech), DsRed2 (Clontech), mStrawberry, TurboFP602 (Evrogen), AsRed2 (Clontech), mRFP1, J-Red, mCherry, HcRed1 (Clontech), Katusha, Kate (Evrogen), TurboFP635 (Evrogen), mP!um, and mRaspberry.

It is to be noted that, in some embodiments, each of the labeling agents (e.g., fluophores) is attached to the DNA molecule by means of click chemistry and that the reagents used for the reaction are derivatives of the labeling agent, which include a reactive group as described herein.

Exemplary fluorescent agents include, but are not limited to, ALEXA FLUOR@dyes, Cy Dyes, Atto dyes, TAMRA dyes, etc., such as, for example, described in the Examples section that follows.

According to some embodiments of the invention, analyzing 5hmC content is done without subjecting the DNA molecule to fragmentation.

As mentioned, the DNA molecule is immobilized on a solid phase.

According to some embodiments of the invention, the extending is linearly extending.

According to some embodiments of the invention, the extending is effected by depositing the DNA molecule on a surface or extending the DNA molecule in a nanochannel.

As used herein "extended DNA molecule" or "elongated DNA molecule" which is interchangeably used herein refers to a single or plurality elongated and fixed (i.e., immobilized) DNA.

According to some embodiments of the invention, the extended DNA molecules are elongated and fixed in a controllable manner directly onto a solid, planar surface. According to a specific embodiment, this solid, planar surface contains a positive charge density which has been controllably modified such that the single nucleic acid molecules will exhibit an optimal balance between the critical parameters of nucleic acid elongation state, degree of relaxation stability and biological activity. Further, methods, compositions and assays are described by which such an optimal balance can precisely and reproducibly be achieved.

According to alternative or additional embodiments, the single nucleic acid molecules are elongated via flow-based techniques. In such an embodiment, a single nucleic acid molecule is elongated, manipulated (via, for example, a regio-specific restriction digestion), and/or analyzed in a laminar flow elongation device. Such a laminar flow elongation devices and methods of elongating or extending DNA are described in U.S. Patent Application 20030124611, which is hereby incorporated by reference in its entirety.

The elongated, individual labeled DNA molecules can then be utilized in a variety of ways which have applications for the analysis of nucleic acid at the genome level. For example, such nucleic acid molecules may be used to generate ordered, high resolution single nucleic acid molecule restriction maps. This method is referred to herein as "optical mapping" or "optical restriction mapping". Additionally, methods are presented whereby specific nucleotide sequences present within the elongated nucleic acid molecules can be identified. Such methods are referred to herein as "optical sequencing". The optical mapping and optical sequencing techniques can be used independently or in combination on the same individual nucleic acid molecules.

Additionally, methods are also presented for the imaging and sizing of the elongated single nucleic acid molecules. These imaging techniques may, for example, include the use of fluorochromes, microscopy and/or image processing computer software and hardware.

Further description of DNA extension is provided hereinbelow and in the Examples section which follows.

According to some embodiments of the invention, step (b, extending) is effected following step (a, attaching to the DNA molecule a 5hmc specific labeling agent). However, it will be appreciated that extending the DNA molecule can be done prior to step (a).

According to some embodiments of the invention, the method further comprises attaching to the DNA molecule an additional labeling agent distinct of the 5hmc specific labeling agent.

According to some embodiments of the invention, the additional labeling agent is an epigenetic modification specific labeling agent. Examples of such modifications include but are not limited to 5-methylcytosine (5mC), histone acetylation and the like.

According to some embodiments of the invention, the additional labeling agent is a non-epigenetic modification specific labeling agent. Examples of such stains and dyes include DNA fluorescent dyes such as cyanine nucleic acid stains, which are essentially nonfluorescent in the absence of nucleic acids and exhibit significant fluorescence enhancements upon DNA binding. The stain may be cell permeant or impermeant.

Such stains are available from Molecular Probes™ (e.g., YOYO™-1. TOTO™ SYTOX™, POPO™-1, BOBO™-1, LOLO™-1, JOJO™-1 etc.). Alternatively, non-fluorescent stains can be used as further described hereinbelow.

Still further, high throughput methods for utilizing such single nucleic acid molecules in genome analysis are presented. In one embodiment of such high throughput methods, rapid optical mapping approaches are described for the creation of high-resolution restriction maps. In such an embodiment, single nucleic acid molecules are elongated, fixed and gridded to high density onto a solid surface. These molecules can then be digested with appropriate restriction enzymes for the map construction. In an alternative embodiment, the single nucleic acid molecules can be elongated, fixed and gridded at high density onto a solid surface and utilized in a variety of optical sequencing-based diagnostic methods. In addition to speed, such diagnostic grids can be reused. Further, the high throughput and methods can be utilized to rapidly generate information derived from procedures which combine optical mapping and optical sequencing methods.

According to an aspect of some embodiments of the present invention there is provided a method of in-situ imaging a DNA molecule, the method comprising:
(a) attaching a labeling agent to the DNA molecule as described herein; and
(b) subjecting the DNA molecule to an imaging method suitable for detecting the labeling agent.

According to some embodiments of the invention, the labeling agent is a fluorescent agent, as described herein, and the imaging method is a fluorescence imaging.

Other labeling agents, as described herein, are also contemplated and respective imaging methods are utilized accordingly.

According to some embodiments of the invention, the method further comprises generating an optical image of the DNA molecule following the imaging.

According to an aspect of some embodiments of the present invention there is provided an extended DNA molecule comprising at least one 5hmc-specific labeling agent.

According to an aspect of some embodiments of the present invention there is provided a DNA molecule comprising at least two different labeling agents, wherein a first labeling agent of the at least two different labels is a 5hmc-specific labeling agent.

According to some embodiments of the invention, the 5hmc-specific labeling agent is attached to the DNA molecule by reacting a labeling agent derivatized by a second reactive group with a DNA molecule in which the 5-hydroxymethylcytosines are glycosylated by a glucose molecule derivatized by a first reactive group,
wherein the first and second reactive groups are chemically compatible to one another, as described in any one of the embodiments pertaining to attaching a 5hmc-specific labeling agent to a DNA molecule of the present invention.

According to some embodiments of the invention, one the first and second reactive groups is azide and the other is alkyne, such that attaching the labeling agent to the DNA molecule is effected by a click chemistry, as described herein.

According to some embodiments of the invention, a second labeling agent of the at least two different labeling agents is a 5mc-specific labeling agent.

According to some embodiments of the invention, a second labeling agent of the at least two different labeling agents is for an epigenetic modification.

According to some embodiments of the invention, a second labeling agent of the at least two different labeling agents is for a non-epigenetically modified base.

As used herein "distinct" or "different" labels refer to labels which can be distinguished upon visualization. Thus in fluorescence labeling one label may be red fluorescence while the other can be blue fluorescence.

According to some embodiments of the invention, the DNA molecule is extended.

According to an aspect of some embodiments of the present invention there is provided a composition-of-matter comprising the DNA molecule.

According to some embodiments of the invention, the DNA molecule is surface deposited or extended in a microchannel.

The present invention also envisages detecting 5hmC in non-immobilized biological samples.

Thus, according to an aspect of some embodiments of the present invention there is provided a method of detecting 5-hydroxymethyl-cytosine (5hmC) in a DNA sample the method comprising:

(a) reacting the DNA sample with a 5hmc-specific fluorescent agent under conditions which allow staining of the DNA sample with said 5hmc-specific labeling agent so as to obtain a 5hmC-labeled DNA sample; and (b) measuring fluorescence intensity of said 5hmC-labeled DNA sample (X) and absorption intensity of the DNA, at 260 nm (Y), wherein a ratio between X to Y is indicative of presence or level of 5hmC in the DNA sample.

As used herein the term "fluorescence intensity" refers to the intensity of the fluorescent probe.

It will be appreciated that for cyanine staining, changes in probe concentration, by dilution of the sample, for example, can, influence the fluorescence intensity of the DNA due to the change in equilibrium. For this reason, DNA preparations are typically not washed to remove unbound probe; otherwise the equilibrium will be interrupted. It will be appreciated that the unbound probe typically does not fluoresce and, hence, demonstrates low background fluorescence. The intensity is measured at an excitation and emission values which depend on the probe.

As used herein "absorbance" refers to DNA light absorbance at 260 nm which is a measure for DNA quantity. At this wavelength, DNA typically exhibits absorbance maxima.

According to a specific embodiment, the ratio is compared to a ratiometric calibration curve.

The calibration curve can be generated by using DNA samples of known percentage of 5hmC labeled using the same methodology as the test DNA sample.

The methodology described herein, according to some embodiments of the present invention can be used to detect global 5hmC modification.

As used herein "global 5hmC modification" refers to the detection of 5hmC of a plurality of DNA molecules which are in a non-immobilized state. The sample may be a heterogeneous sample.

According to a specific embodiment, this methodology is more sensitive than absorption measurement of labeled 5hmC. Thus as shown in Example 2 of the Examples section which follows, measuring the ratio between the fluorescence signal of labeled 5hmC and the absorption of DNA at 260 nm allowed to detect down to 0.004% 5hmC/dN from a sample extracted from liver, with a sample concentration of 136 ng/µl in 20 µl volume and 0.02% 5hmC/dN from a DNA sample concentration of only 82 ng/µl in 20 µl volume (1.6 µg), see FIGS. 5A-5B.

It is contemplated that the threshold of sensitivity or the limit of detection is about 0.0022% 5hmC/dN.

The concentration of the DNA in the test sample depends on the level (e.g., %) of hmC in the tissue. Thus, a higher DNA concentration is required for tissues with lower levels hmC. In general when assayed using a plate reader, the concentration of DNA that can be read is up to 350 ng/µl DNA without having signal saturation (e.g., 1-350 ng/µl). This concentration of DNA is high enough for detection % hmC at low-% hmC-containing tissues such as spleen and liver. However for tissues containing even lower % hmC, concentrated DNA samples (e.g., 100 ng/µl to 100 µg/µl) may be measured for their fluorescence intensity and then diluted for measuring their DNA concentration. 1 pg-/µl-100 µg/µl, 1 pg/µl-50 µg/µl, e.g., 5 ng/µl-5 µg/µl.

According to a specific embodiment, the volume of the sample is between 5-50 µl or 10-20 ul for the detection of hmC in genomic DNA in multi well plate.

Once the level of 5hmC modification has been determined, the sample can be subjected to optical imaging by extending the molecules on slides (immobilizing the DNA molecules) as described herein. Alternatively, the position of the modification can be analyzed using enzymes which are sensitive to bulky residues i.e., the modification of the 5hmC with $N_3$-5-gmC.

Presence of $N_3$-5-g group on the DNA template strand will interfere with the synthesis of a nucleic acid strand by DNA polymerase or RNA polymerase, or the efficient cleavage of DNA by a restriction endonuclease (e.g., Msp1) or inhibition of other enzymatic modifications of nucleic acid containing 5-hmC. As a result, primer extensions or other assays can be employed, for example, to evaluate a partially extended primer of certain length and the modification sites can be revealed by sequencing the partially extended primers.

The ability to sensitively and specifically detect 5hmC modifications can be harnessed for large scale settings in which hundreds (e.g., 300-5000) or thousands of DNA samples are analyzed using an automated equipment.

In certain aspects, differential modification of nucleic acid between two or more samples can be evaluated.

In such differential analysis studies, global DNA samples of different tissues, age, gender, medical conditions (diseased vs healthy) can be analyzed.

Alternatively, specific DNA sequences of the aforementioned types can be analyzed.

Studies including heart, liver, lungs, kidney, muscle, testes, spleen, and brain indicate that under normal conditions 5-hmC is predominately in normal brain cells. Additional studies have shown that 5-hmC is also present in mouse embryonic stem cells. The Ten-eleven translocation 1 (TET1) protein has been identified as the catalyst for converting 5-mC to 5-hmC. Studies have shown that TET1 expression is inversely correlated to 5-mC expression. Overexpression of TET1 in cells seems to correlate with increased expression of 5-hmC. Also, TET1 is known to be involved in pediatric and adult acute myeloid leukemia and acute lymphoblastic leukemia. Thus, evaluating and comparing 5-hmC levels can be used in evaluating various disease states and comparing various nucleic acid samples.

Thus the output of such methods can be used in a variety of research and clinical applications such as in diagnostics, therapy and drug development.

According to an additional aspect of the present invention there is provided a computer readable storage medium comprising a database including a plurality of DNA sequences and information pertaining to 5hmC modification of the plurality of DNA molecules.

Thus, the computer readable storage medium may comprise information pertaining to the position of the 5hmC modification on the DNA sequence, the level of 5hmC, the tissue distribution of a given 5hmC modification on a DNA molecule. The database further includes information pertaining to the DNA sequence such as annotation, transcribed/translated mRNA/protein sequence, post translational modifications and the like.

According to still further features in the described preferred embodiments the database further includes information pertaining to generation of the database and potential uses of the database.

According to an aspect of some embodiments of the present invention there is provided a method of preparing UDP-6-N$_3$-Glucose, the method comprising subjecting an azido glucose (6-azido glucose) an enzymatic catalysis by kinase N-acetylhexoseamine 1-kinase (NahK), in the presence of ATP to thereby obtain a phosphorylated 6-azidoglucose; and subjecting the phosphorylated 6-azido glucose to enzymatic catalysis by uridyltransferase (GlmU) in the presence of UTP.

According to an aspect of some embodiments of the present invention there is provided a method of preparing UDP-6-N$_3$-Glucose, as depicted in FIG. 1.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

The phrase "covalent bond", as used herein, refers to one or more pairs of electrons which are shared between atoms in a form of chemical bonding.

The term "amide" describes a —NR'—C(=O)— linking moiety, where each of R' and R" is independently hydrogen, alkyl, cycloalkyl, heteroalicyclic, aryl or heteroaryl, as these terms are defined herein.

The term "carboxylate" or "ester", as used herein, refers to a —C(=O)—O—R' end group, where R' is as defined herein, or a —C(=O)—O— linking moiety.

The term "triazine" refers to a heterocyclic ring, analogous to the six-membered benzene ring but with three carbons replaced by nitrogen atoms. The three isomers of triazine are distinguished from each other by the positions of their nitrogen atoms, and are referred to as 1,2,3-triazine, 1,2,4-triazine, and 1,3,5-triazine. Other aromatic nitrogen heterocycles include pyridines with 1 ring nitrogen atom, diazines with 2 nitrogen atoms in the ring and tetrazines with 4 ring nitrogen atoms.

The term "triazole" refers to either one of a pair of isomeric chemical compounds with molecular formula $C_2H_3N_3$, having a five-membered ring of two carbon atoms and three nitrogen atoms, namely 1,2,3-triazoles and 1,2,4-triazoles.

The term "disulfide" refers to a —S—S— linking moiety.

The term "imine", which is also referred to in the art interchangeably as "Schiff-base", describes a —N=CR'— linking moiety, with R' as defined herein or hydrogen. As is well known in the art, Schiff bases are typically formed by reacting an aldehyde or a ketone and an amine-containing moiety such as amine, hydrazine, hydrazide and the like, as these terms are defined herein. The term "aldimine" refers to a —CH=N— imine which is derived from an aldehyde. The term "ketimine" refers to a —CR'=N— imine which is derived from a ketone.

The term "hydrazone" refers to a —R'C=N—NR" linking moiety, wherein R' and R" are as defined herein.

The term "semicarbazone" refers to a linking moiety which forms in a condensation reaction between an aldehyde or ketone and semicarbazide. A semicarbazone linking moiety stemming from a ketone is a —R'C=NNR"C(=O)NR'"—, and a linking moiety stemming from an aldehyde is a —CR'=NNR"C(=O)NR'" wherein R' and R" are as defined herein and R'" or as defined for R'.

As used herein, the term "lactone" refers to a cyclic ester, namely the intra-condensation product of an alcohol group —OH and a carboxylic acid group —COOH in the same molecule.

As used herein, the term "lactam" refers to a cyclic amide, as this term is defined herein. A lactam with two carbon atoms beside the carbonyl and four ring atoms in total is referred to as a β-lactam, a lactam with three carbon atoms beside the carbonyl and five ring atoms in total is referred to as a γ-lactam, a lactam with four carbon atoms beside the carbonyl and six ring atoms in total is referred to as a δ-lactam, and so on.

As used herein, the term "aldehyde" refers to an —C(=O)—H group.

The term "hydroxy" as used herein describes an —OH group.

The terms "thio", "sulfhydryl" or "thiohydroxy" as used herein describe an —SH group.

The term "disulfide" as used herein describes an —S—S— linking moiety.

The term "alkoxy" as used herein describes an —O-alkyl, an —O-cycloalkyl, as defined hereinabove. The ether group —O— is also a possible linking moiety.

The term "aryloxy" as used herein describes an —O-aryl group.

The term "thioalkoxy" as used herein describes an —S-alkyl group. The thioether group —S— is also a possible linking moiety.

The term "thioaryloxy" as used herein describes an —S-aryl group. The thioarylether group —S-aryl- is also a possible linking moiety.

As used herein, the term "amine" refers to an —NR'R" group where R' and R" are each hydrogen, alkyl, alkenyl, cycloalkyl, aryl, heteroaryl (bonded through a ring carbon) or heteroalicyclic (bonded through a ring carbon) as defined hereinbelow.

The terms "halide" or "halo" refer to fluorine, chlorine, bromine or iodine.

As used herein, the term "azide" refers to a —$N_3$ (—N=$N^+$=$N^-$) group.

The term "aziridine", as used herein, refers to a reactive group which is a three membered heterocycle with one amine group and two methylene groups, having a molecular formula of —$C_2H_3NH$.

The term "diene", as used herein, refers to a —CR'=CR"—CR'"=CR"" group, wherein R' as defined hereinabove, and R" R'" and R"" are as defined for R'.

The term "dienophile", as used herein, refers to a reactive group that reacts with a diene, typically in a Diels-Alder reaction mechanism, hence a dienophile is typically a double bond or an alkenyl.

The term "epoxy", as used herein, refers to a reactive group which is a three membered heterocycle with one oxygen and two methylene groups, having a molecular formula of —$C_2H_3O$.

The term "azo" or "diazo" describes an —N=NR' reactive group or an —N=N-linking moiety, as these phrases are defined hereinabove, with R' as defined hereinabove.

The term "carbamate" refers to a —NR'(C=O)OH (carbamic acid) end or reactive group, or a —NR'(C=O)O— linking moiety, with R' as defined hereinabove.

The term "thiocarbamate" refers to a —NR'(C=S)OH end or reactive group, or a —NR'(C=S)O— linking moiety, with R' as defined hereinabove.

The term "carbonyl" refers to a —(C=O)— group.

The term "thiocarbonyl" refers to a —(C=S)— group.

As used herein, the term "carboxyl" refers to an —C(=O)OH group.

The term "cyano" describes a —C≡N group.

The term "isocyanate" describes an —N=C=O group.

The term "hydrazide", as used herein, refers to a —C(=O)—NR'—NR"R'" group wherein R', R" and R'" are each independently hydrogen, alkyl, cycloalkyl or aryl, as these terms are defined herein.

As used herein, the term "hydrazine" describes a —NR'—NR"R'" group, wherein R', R" and R'" are each independently hydrogen, alkyl, cycloalkyl or aryl, as these terms are defined herein.

The term "hydroxylamine", as used hereon, refers to either a —NHOH group or a —$ONH_2$.

The term "nitro" describes an —$NO_2$ group.

The term "acyl halide" describes a —(C=O)R"" group wherein R"" is halide, as defined hereinabove.

The term "phosphate" describes an —O—P(=O)$_2$(OR') end or reactive group or a —O—P(=O)$_2$(O)— linking moiety, as these phrases are defined hereinabove, with R' as defined herein.

The term "phosphonate" describes a —P(=O)(OR') (OR") end or reactive group or a —P(=O)(OR')(O)— linking moiety, as these phrases are defined hereinabove, with R' and R" as defined herein.

The term "sulfoxide" or "sulfinyl" describes a —S(=O) R' end or reactive group or an —S(=O)— linking moiety, as these phrases are defined hereinabove, where R' is as defined hereinabove.

The term "sulfonamide" encompasses the term "S-sulfonamide" which describes a —S(=O)$_2$—NR'R" end or reactive group or a —S(=O)$_2$—NR'— linking moiety, as these phrases are defined hereinabove, with R' and R" as defined herein; and the term "N-sulfonamide" which describes an R'S(=O)$_2$—NR"— end or reactive group or a —S(=O)$_2$—NR'— linking moiety, as these phrases are defined hereinabove, where R' and R" are as defined herein.

The term "sulfonate" describes a —S(=O)$_2$—R' end or reactive group or an —S(=O)$_2$— linking moiety, as these phrases are defined hereinabove, where R' is as defined herein.

As used herein, the term "alkyl" describes an aliphatic hydrocarbon including straight chain and branched chain groups. Preferably, the alkyl group has 1 to 20 carbon atoms, and more preferably 1-10 carbon atoms. Whenever a numerical range; e.g., "1-10", is stated herein, it implies that the group, in this case the alkyl group, may contain 1 carbon atom, 2 carbon atoms, 3 carbon atoms, etc., up to and including 10 carbon atoms. The alkyl can be substituted or unsubstituted. When substituted, the substituent can be, for example, an alkyl, an alkenyl, an alkynyl, a cycloalkyl, an aryl, a heteroaryl, a halide, a hydroxy, an alkoxy and a hydroxyalkyl as these terms are defined hereinbelow.

The term "alkenyl" describes an unsaturated alkyl, as defined herein, having at least two carbon atoms and at least one carbon-carbon double bond. The alkenyl may be substituted or unsubstituted by one or more substituents, as described for alkyl hereinabove.

The terms "alkynyl" or "alkyne", as defined herein, is an unsaturated alkyl having at least two carbon atoms and at least one carbon-carbon triple bond. The alkynyl may be substituted or unsubstituted by one or more substituents, as described hereinabove.

The term "cycloalkyl" describes an all-carbon monocyclic or fused ring (i.e., rings which share an adjacent pair of carbon atoms) group where one or more of the rings does not have a completely conjugated pi-electron system. The cycloalkyl group may be substituted or unsubstituted as described for alkyl hereinabove.

The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted as described for alkyl hereinabove. Representative examples are piperidine, piperazine, tetrahydrofurane, tetrahydropyrane, morpholino and the like.

The term "aryl" describes an all-carbon monocyclic or fused-ring polycyclic (i.e., rings which share adjacent pairs of carbon atoms) groups having a completely conjugated pi-electron system. The aryl group may be substituted or unsubstituted. Substituted aryl may have one or more substituents as described for alkyl hereinabove.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted as described for alkyl hereinabove. Representative examples of heteroaryls include triazole, furane, imidazole, indole, isoquinoline, oxazole, pyrazole, pyridine, pyrimidine, pyrrole, quinoline, thiazole, thiophene, triazine, purine and the like.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non limiting fashion. Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

5hmC Labeling

Material and Experimental Methods

Synthesis of UDP-6-azide Glucose:

The T4 bacteriophage uses the enzyme β-glucosyltransferase (β-GT) to glucosilate hydroxylated bases in its DNA. Recently, a selective chemical method for the labeling of 5hmC was developed. In this method β-GT was exploited in order to transfer an azide-substituted glucose (UDP-6-$N_3$-Glu) onto the hydroxyl group of 5hmC to form β-6-azide-glucosyl-5-hydroxymethyl-cytosine (5-$N_3$-gmC). The presence of an azido moiety paves the way for 5hmC labeling using a click chemistry reaction by the addition of an alkyne substituted dye.

The main bottleneck of this labeling process is the cofactor UDP-6-$N_3$-Glu, which can be synthesized or purchased but with very high costs.

Herein, an enzymatic approach is used in order to have high yields of UDP-$N_3$-Glu. A glucose azide (see FIG. 1) is used as a substrate for a sequential enzymatic cascade.

The glucose azide can be synthesized as described in FIG. 1, and then be subjected to the following reactions: a) First, the kinase N-acetylhexoseamine 1-kinase (NahK) is used to add a phosphate group to the glucose, using ATP as a co-factor and b) Second, an uridyltransferase (GlmU) is used with UTP as a cofactor to catalyze conjugation of a UDP group to form the desired UDP-$N_3$-Glu.

NahK and GlmU are purified as discussed previously (Chen et al., 2011).

DNA Samples:

5hmC-saturated DNA fragments of 1 kb and 70 bp were prepared by PCR amplification of lambda DNA (New England Biolabs; (NEB), Ipswich MA, USA), using the following primers: forward primer: 5-CTCATGCT-GAAAACGTGGTG-3 (SEQ ID NO: 1), reverse primer: 5-GGACAGGACCAGCATACGAT-3 (SEQ ID NO: 2) and forward primer: 5-/5Alex488N/TAAATTAGTTACACAG-GAAA-3 (SEQ ID NO: 3) reverse primer: 5-AAGCCACAA CTCTAATTTT-3 (SEQ ID NO: 4) for 1 kb and 70 bp DNA fragments, respectively (Integrated DNA Technologies Inc, Coralville, IA USA). A typical reaction was performed in a volume of 50 μl, and contained 200 ng of template DNA, 2 units of Vent (exo-) (NEB), 200 μM of dAGT (Sigma-Aldrich Israel Ltd. Rehovot, Israel) and 5hmC (Bioline Reagents Ltd., London, UK) nucleotides in NEB thermopol buffer. Reaction mixtures were incubated at 95° C. for 2 minutes as an initial step, followed by 30-35 cycles of 30 seconds at 95° C., 30 seconds at 55° C. and 2 minutes at 72° C. or 30 seconds at 95° C., 30 seconds at 42° C. and 30 seconds at 72° C. for the 1 kb and 70 bp products, respectively, and finally 5 minutes at 72° C.

For the analysis of the labeling efficiency of 5 hmC, the 70 bp lambda DNA fragments were prepared with ALEXA FLUOR® 647-dCTP (Molecular Probes, Eugene, OR, USA) instead of 5hmC. The reaction was performed in a volume of 50 μl, and contained 200 ng of template DNA, 2 units of Vent (exo-), 50 μM of dATP dGTP and dTTP and 50 μM ALEXA FLUOR® 647-dCTP nucleotides in NEB thermopol buffer. Reaction mixtures were incubated at 95° C. for 2 minutes as an initial step, followed by 35 cycles of 30 seconds at 95° C., 30 seconds at 42° C. and 30 minutes at 50° C., and finally 10 minutes at 72° C. This control ALEXA FLUOR® 647-PCR product contained three cytosine sites and represents 100% labeling efficiency. All PCR products were cleaned of free nucleotides and primers using QIAquick PCR purification kit (QIAGEN GmbH, Hilden, Germany).

For extraction of DNA from mouse tissues, 5 prime ArchivePure DNA cell/tissue kit was used according to manufacturer's instructions.

Preparation of Hydroxymethylated Lambda DNA by Sequence Specific Labeling:

Lambda phage intact genomes (48.5 kb) were labeled with 5hmC nucleotides by nick translation[1]. 10 μg of DNA was incubated with 10 u/μg Nt.BspQI (NEB) nicking enzyme in 100 μl NEB buffer 3 for 2 h at 50° C., followed by heat inactivation for 20 min at 80° C. For labeling of the DNA, nicked DNA was incubated for 2 h at 72° C. in 200 μl NEB thermopol buffer with 2 u/μg Vent (exo-) and 250 nM dNTPs. For incorporation of hydroxymethyl, DNA was incubated with 250 nM dATP dGTP and dTTP and 250 nM of 5-hydroxymethyl-labeled cytosine (Bioline).

Fluorescent-Labeling of 5hmC by Click Chemistry:

In the case of lambda DNA for single molecule optical mapping, 10 μg of Nt.BspQI site Hydroxymethylated DNA in 50 mM Hepes (Sigma-Aldrich Israel Ltd.) was incubated with 20 units of T4-beta-glucosyltransferase (NEB) for glucosylation of 5hmC, in the presence of NEB buffer 4 and 150 μM UDP-azide glucose (Active Motif, Carlsbad, CA, USA), for 2 hours at 37° C. As a control reaction, UDP-azide glucose was replaced by UDP-glucose at the same molar concentration. The click chemistry reaction was performed, copper-free, by the addition of 250 μM ALEXA FLUOR® 555 DIBO alkyne (Molecular Probes) for 1 hour at 37° C. Buffer was then exchanged to 50 mM Hepes, and sample was stained with 1 μM YOYO-1.

For labeling 5hmC-saturated PCR products, 1-3 μg was first glucosylated by incubation with UDP-glucose-azide (Active Motif) at a molar ratio of 1:30 (5hmC: UDP-glucose-azide) and 50 units of T4-beta-glucosyltransferase (NEB), in the presence of NEB buffer 4, overnight at 37° C. Two types of click reactions were used: First, a copper-free reaction, with ALEXA FLUOR® 647-DIBO (dibenzocyclooctyne) alkyne (Molecular Probes) (for the 1 kb PCR product) at a molar ratio of 1:100 (5hmC: DIBO) in 10 mM PBS. Second, a copper-dependent reaction with ALEXA FLUOR® 647-alkyne at a molar ratio of 1:100 (5hmC: alkyne) in the presence of 200 mM triethylammonium acetate buffer, 50% DMSO, freshly prepared 0.5 mM ascorbic acid and 0.5 mM Cu-TBTA (Tris[(1-benzyl-1H-1,2,3-triazol-4-yl)methyl]amine complex in 55% DMSO. The copper in the second reaction served as a catalyst which was not required when using cyclooctynes as in the DIBO alkyne. Both reactions were incubated at 22° C. overnight. The reaction sample was degassed by nitrogen before addition of Cu-TBTA complex and flashed before incubation. As a control reaction, UDP-glucose- azide was replaced by UDP-glucose at the same molar concentration.

Each incubation step preceded a purification step with Qiagen PCR purification columns (QIAGEN).

Using the synthetic pathways described hereinabove, click chemistry syntheses were performed for labeling 5-hmC, using the following alkyne-containing fluofhores:

DBCO-Cy5 (Dibenzylcyclooctyne-Sulfo-Cy5, Gena Bioscience); BCN Cy5 [N. J. Agard, J. A. Prescher and C. R. Bertozzi, J. Am. Chem. Soc., 2004, 126, 15046; (b) N. J. Agard, J. M. Baskin, J. A. Prescher, A. Lo and C. R. Bertozzi, ACS Chem. Biol., 2006, 1, 644; (c) J. M. Baskin, J. A. Prescher, S. T. Laughlin, N. J. Agard, P. V. Chang, I. A. Miller, A. Lo, J. A. Codelli and C. R. Bertozzi, Proc. Natl. Acad. Sci. U.S.A, 2007, 104, 16793; (d) S. T. Laughlin, J. M. Baskin, S. L. Amacher and C. R. Bertozzi, Science, 2008, 320, 664; (e) E. M. Sletten and C. R. Bertozzi, Org. Lett., 2008, 10, 3097, BCN-amine was purchased from Sigma-Aldrich Cat #745073 and coupled cy5-NHS ester, Fischer Scientific Cat #45-001-190]; DBCO-TAMRA (Dibenzylcyclooctyne-PEG$_4$-5/6-Tetramethylrhodamine, Gena Bioscience).

5hmC Quantification by UV-Vis Spectroscopy:

In order to determine the percentage of 5hmC in an examined DNA sample, a calibration curve was obtained with a DNA sample that contains a known 5hmC percentage. For this purpose, ALEXA FLUOR® 647-5hmC labeled-1 kb PCR product was mixed with increasing concentrations of non-labeled XL1 bacteria plasmids and the absorption ratio at 260 nm for DNA and 647 nm for labeled 5hmC was plotted. Increasing amounts of plasmids (600, 1200 and 1750, 3500 ng) were added to fixed amounts of 5hmC-saturated 1 kb lambda fragments (in the order of 4 and 2 ng). The 1 kb fragment contained 29% 5hmC and was fluorescently labeled by the click reaction. Plasmids were extracted from a XL1 PE bacteria by a DNA purification system (Promega, Madison WI, USA). Absorption measurements were conducted on a NanoPhotometer® P 300 (IMPLEN, Munich, Germany).

Analysis of Labeling Efficiency:

ALEXA FLUOR® 488-labeled-70 bp PCR products that were prepared with ALEXA FLUOR® 647-dCTP nucleotides, or with 5hmC nucleotides, were used. The 5hmC product was subjected to click reaction and the two sets of DNA samples were analyzed by electrophoresis and run side by side through a 3% agarose gel, in TBE buffer, at 80 volts. The gel was imaged on a multicolour laser gel scanner, GE Healthcare FLA5000. A normalization of the DNA amount loaded on the gel was achieved by comparing the fluorescence intensity of the 70 bp bands at 510 nm, resulting from the ALEXA FLUOR® 488 molecule bound to the forward primer of both control and click reaction products, following excitation with 473 nm laser. The efficiency of the click labeling procedure was calculated by comparing the bands fluorescence intensity at 665 nm, resulting from the ALEXA FLUOR®-labeled dC nucleotides or 5hmC subjected to a click reaction, following excitation with 635 nm laser. Fluorescence intensity measurements were analyzed by ImageJ: www(dot)rsbweb(dot)nih(dot)gov/ij/.

DNA Extension:

Surfaces for DNA extensions were prepared according to Sidorova et al.[2] with minor modifications. Briefly, 24×24 glass cover slips were cleaned by 7 hours to overnight incubation in a freshly made 2:1 (v/v) mixture of nitric acid (70%) and hydrochloric acid (37%). The incubation proceeded in a chemical fume hood and was followed by an extensive wash with ultrapure water (18 MΩ), ethanol and dried under a stream of nitrogen. Dry slides were immersed in a premixed solution containing 595 μl N-trimethoxysilylpropyl-N,N,N-trimethylammonium chloride and 216 μl of vinyltrimethoxysilane in 300 ml ultrapure water and incubated overnight at 65° C. After incubation, slides were thoroughly washed with ultrapure water and ethanol and stored at 4° C. in ethanol. The silane solution was freshly made and thoroughly mixed before the slides were introduced into the mixture. Stored slides were normally used within 2 weeks. Lambda DNA molecules were extended on silanized glass slides by placing a 5 µl drop of pre-labeled Lambda DNA in 50 mM HEPES buffer and 200 mM dithiothreitol (DTT) in-between a dry silanized glass slide and a non-treated microscope glass slide (lambda DNA concentration was as appropriate for single molecule imaging).

Data Acquisition and Analysis:

Extended DNA molecules were imaged on a MORE imaging system (TILL photonics GmbH, Munich, Germany) with an Olympus UPlanApo 60X 1.35 NA oil immersion objective. A 150 W Xenon lamp with galvanometer driven filter switching was used as an excitation source. The filter sets used to image YOYO-1 stained DNA and the ALEXA FLUOR® 555 labels were 482/18 and 561/14 bandpass excitation filters, 405/488/561/640 quadband beamsplitter and a 446/523/600/677 quadband emission filter (all from Semrock, Rochester, NY, USA). Images were acquired by a DU888 EMCCD (Andor, Belfast, Ireland) with an EM gain setting of 200 and integration times of 200 ms and 1300 ms for YOYO-1 and ALEXA FLUOR® 555 respectively.

The positions of the ALEXA FLUOR® 555 fluorescence spots along the DNA were mapped in order to verify that they are located in the expected positions of 5hmC sites. In order to determine the genomic position of the tags the distance (in pixels) between the Tag signal position and the far end of the DNA was measured. This value was divided by the measured full length of the DNA to give a normalized position value (ranging from 0 to 100). Fluorescence spots were mapped manually using a Matlab program written for this purpose. The spectrally separated images of the stretched DNA and of the ALEXA FLUOR® 555 fluorescent spots were overlaid to visualize fluorescent tags bound on the hydroxymethylated DNA bases. Using the Matlab function Improfile, a line was manually drawn along each long DNA strand (>80 pixels) that showed at least four fluorescent spots along its contour and had orientation that was clearly evident from the spot pattern. The Improfile function projects the intensity values of each pixel along the drawn line on a pixel vs. intensity plot. The DNA lengths were measured by subtracting the two y-intercepts on the DNA channel that represent DNA ends. Fluorescence spots generated by labeled 5hmC bases may be accurately localized by 2D Gaussian fittingE[3,4]. Images were analyzed using a custom Matlab program that extracts the position coordinates of fluorescent spots. After localizing each spot, its distance to one end of the DNA was measured in order to assign a genomic position. In order to account for the large variation in stretching factor between different DNA molecules the measured locations were normalized to units of percentage of the whole genome (100% representing the far end of the phage genome at 48500 base pairs). By dividing the distance of the tag location from the DNA end point by the total length of the template DNA molecule, a normalized value for all detected tags is calculated, allowing statistical analysis of the pooled data as shown hereinbelow.

Experimental Results

β-GT was used to tag 5hmC sites with a fluorescent reporter molecule (labeling agent). The enzyme was fed with a synthetic cofactor UDP-6-$N_3$-Glu, resulting in covalent attachment of a functional azide at the 5hmC site (FIG. 2). This azide was further reacted with an ALEXA FLUOR® alkyne via a "click" chemistry reaction to generate the fluorescently labeled 5hmC (FIG. 2). The resulting DNA product had fluorescence and absorbance proportional to the content of 5hmC residues.

To demonstrate the viability of such an approach 10 specific 5hmC sites within the 48.5-kb genome of lambda bacteriophage were engineered. Hydroxymethylated cytosine nucleotides were incorporated by a DNA polymerase (Vent exo-) into nicks induced along the genome at GCTCTTC (SEQ ID NO: 5) sites by the endonuclease BspQI. The hydroxymethylated sites along the DNA were labeled after glucosylation with ALEXA FLUOR® 555. The DNA was stained with YoYo-1 intercalating dye and extended on modified glass surfaces for imaging[13]. Dual-color fluorescence images of the sample revealed that the lambda phage DNA was decorated with fluorescent spots (FIG. 3B). In order to map the positions of the spots along the DNA and correlate them with the expected 5hmC pattern, only molecules that were more than 80 pixels long were analyzed. This length corresponds to a minimum threshold of 70% extension relative to the 17 µm, full length of the genome. At this extension the labels maintained their relative positions, and labeling could be quantitatively assessed. The expected pattern and several examples of individual genomes decorated with multiple fluorescent spots indicating 5hmC sites are shown in FIGS. 3A and 3B. The expected 5hmC pattern is clearly reconstructed by the fluorescent labels, indicating that labeling was highly specific.

For mapping the 5hmC sites, fluorescent spots were localized by 2D-Gaussian fitting and their positions relative to the DNA extremities were measured. To compensate for the poor extension uniformity of the DNA molecules, the positions relative to the full length of the genome were represented as percentages from the whole. Out of the 157 molecules that passed the length threshold, 93 molecules with clearly visible orientations that were labeled at four or more positions along the genome were analyzed. A histogram of all detected fluorescent spots (N=512) shows clear resemblance to the reference map, and multi-peak Gaussian fitting of the histogram is in good agreement with expected positions (FIGS. 3A and 3B).

5hmC was labeled in DNA extracted from mouse brain and kidney (FIGS. 3C and 3D). Both tissues are reported to be relatively rich in 5hmC[16] and fluorescent spots indicating individual hmC residues are clearly seen along the genomic fragments.

To test the efficiency of the labeling procedure, a ratiometric measurement was performed, that compared the fluorescence signal from PCR synthesized DNA containing labeled 5hmC residues to that of identical DNA in which 5hmC bases were substituted with an ALEXA FLUOR® 647 fluorophore. The latter served as a control that represents 100% labeling efficiency. An ALEXA FLUOR® 488 pre-labeled PCR primer was used for the reaction in order to report on the total amount of DNA analyzed. ALEXA FLUOR® 647 was used for the 5hmC labeling. The two sets of DNA molecules were run side by side on a 3% agarose gel, and the fluorescent DNA bands were imaged on a multicolor gel scanner. Band intensity in the green channel, representing the single ALEXA FLUOR® 488 present in all molecules, allowed normalization for the total amount of DNA in the detected bands. The degree of 5hmC labeling was deduced from the fluorescence intensities of the bands in the red channel, by calculating the ratio of ALEXA FLUOR® 647 fluorescence levels between the control and the 5hmC-labeled samples. Analysis of the relative intensity levels indicated a total labeling efficiency of 84%.

Another useful feature of the present labeling scheme is the ability to use a simple UV-Vis spectrophotometer in order to quantify global 5hmC levels in DNA. In the absorption spectrum, both the labeling fluorophore and the DNA bases themselves have a characteristic absorption band that can be used to directly quantify the amount of 5hmC relative to the total DNA content. One example is presented in FIG. 4A. The labeled DNA has an absorbance spectrum featuring distinct maxima at 260 nm (for DNA) and 647 nm (for labeled 5hmC). This potentially provides a sensitive assay for quantifying global 5hmC levels in genomic DNA.

Since 5hmC levels vary greatly between different tissues and different cell lines, with typical values from around 0.01% for HeLa cells and up to 0.65% for hmC/dG human brain tissue[17], it was verified that the method is sensitive enough to access biologically relevant genomic 5hmC content. Four calibration samples with total nucleotide to 5hmC ratios between 1:500 (0.2%) and 1:5000 (0.02%) were prepared and used in the protocol to tag glucosilated 5hmC with ALEXA FLUOR® 647. The concentration of the calibration samples were on the order of 600 to 3500 ng/µL of DNA. Only 1 µl of sample was used for each UV-Vis absorption measurement, requiring amounts of DNA easily obtained from less than 1 mg of tissue by standard DNA extraction kits. After spectra were taken for all samples, a calibration curve was built using the absorption data (FIG. 4B).

FIG. 4B demonstrates a full linearity of the relative absorbance at 260 nm and 647 nm of an ALEXA FLUOR® 647-labeled DNA and the amount of 5hmC in the DNA, indicating that relative absorbance can be used as a sensitive measurement of quantifying 5hmC.

In order to verify that labeling is specific and that no residual absorbance at 647 nm occurs due to non-specific binding, an identical experiment was conducted only substituting the UDP-glucose-azide with a standard UDP-glucose which is not reactive towards the alkyne modified ALEXA FLUOR® 647 dye. No residual absorption was detected in the control sample; indicating that fluorescent labeling of 5hmC residues may provide a rapid and facile mean to quantify total 5hmC content in genomic DNA from various sources.

The measurement is performed on a standard spectrophotometer readily available in most labs and requires small amounts of genetic material. As opposed to previously published techniques that require further timely post-processing such as pull-down, RT-PCR, HPLC or enzymatic signal amplification such as ELISA[18] the reported technique delivers rapid and unambiguous results and lends itself readily to automated analysis in a high-throughput multi-well format.

Example 2

5hmC Labeling is Sensitive and can be Done in High Throughput Settings

Example 1 above establishes the use of some embodiments of the present methodology for the quantification of global % hmC in a given sample. The technique is based on covalent labeling of hmC moieties by an enzymatic reaction, which is followed by the Huisgen cycloaddition of an alkyne to an azide moiety. Fluorescently labeled alkynes are used to fluorescently label hmC so that a ratiometric measurement of the absorption intensities of the fluorophore relative to the DNA, at 260 nm, can be obtained. These measurements were conducted on a nanodrop spectrophotometer. A drop of 1 µl containing 1650 ng/µl of DNA was required in order to detect 0.02% hmC in a given sample. This is a highly concentrated sample which could sometimes be challenging to achieve. Each sample is measured separately since only one drop could be measured at a time.

Following is an improved ratiometric detection method which is based on the ratio between the fluorescence intensity (rather than the absorption) of a hmC-labeled DNA sample and the absorption intensity of the DNA, at 260 nm (FIGS. 5A-5B). The value obtained is compared to a ratiometric calibration curve, prepared in the same manner for samples with known % hmC (FIG. 6A, insert). The fluorescent measurements are more sensitive than the absorption measurements of labeled hmC allowing to detect down to 0.004% hmC/dN from a DNA sample extracted from the liver, with a sample concentration of only 136 ng/ul in 20 µl volume (2.7 µg) and 0.02% hmC/dN from a DNA sample concentration of only 82 ng/ul in 20 µl volume (1.6 µg) (FIG. 6B).

The present methodology was further assessed in high throughput settings. Measurements were conducted on a 384 well multiplate using a multiplate reader Tecan infinit M200. This allows measuring multiple samples in one scan, eliminating errors that may be extracted from instrumental factors.

In addition to global hmC quantifications, it was shown above in Example 1, that it is possible to optically image hmC sites in single DNA fragments, stretched on glass slides. The following experiments have shown that single molecule experiments allows the detection of not only extremely low hmC amounts such as in human peripheral blood mononucleated cell (PBMC) (FIG. 7A) and spleen (FIG. 7B) but also inhomogeneity in the amount or distribution of hmC in DNA fragments extracted from the same tissue sample: DNA extracted from the spleen and from PBMC (FIGS. 7A and 7B) had, in most fragments, very low frequency of hmC labeling (orange arrows), whereas, few fragments had irregularly high hmC labeling (blue arrows). In the brain, most DNA fragments had high hmC labeling (FIG. 7C). This data, which points out for variations within populations could only be detected by single molecule techniques.

Finding regions of enriched hmC moieties on single DNA strands must be accompanied by a system that would allow the identification of the position of these regions within the entire genome, relative to specific genes within different chromosomes. Such system may be based on the creation of a specific DNA signature map of a typical pattern. A signature map or a DNA barcoding may be achieved by sequence-specific nicking enzymes, which make nicks in DNA fragments in positions adjacent to their recognition sights. Further enzymatic nuclear polymerization reaction allows the incorporation of fluorescently labeled nucleotides in the region of the nicked positions, forming a sequence-specific barcoding of DNA strands (FIGS. 8A-8B, green label). FIGS. 8A-8B show DNA strands, stretched on glass slides (Blue) from Zebra fish (A) and from mouse brain (B) that are labeled both for hmC (pink) and for the BsPQI nicking enzyme recognition sites (green), allowing optical mapping of hmC sites.

REFERENCES

Other References are Provided in the Document

1. S. Kriaucionis and N. Heintz, *Science (New York, N.Y.),* 2009, 324, 929-30.
2. M. Tahiliani, K. P. Koh, Y. Shen, W. A. Pastor, H. Bandukwala, Y. Brudno, S. Agarwal, L. M. Iyer, D. R. Liu, L. Aravind, and A. Rao, *Science (New York, N.Y.),* 2009, 324, 930-5.
3. Y.-F. He, B.-Z. Li, Z. Li, P. Liu, Y. Wang, Q. Tang, J. Ding, Y. Jia, Z. Chen, L. Li, Y. Sun, X. Li, Q. Dai, C.-X. Song, K. Zhang, C. He, and G.-L. Xu, *Science (New York, N.Y.),* 2011, 333, 1303-7.
4. C.-X. Song, K. E. Szulwach, Y. Fu, Q. Dai, C. Yi, X. Li, Y. Li, C.-H. Chen, W. Zhang, X. Jian, J. Wang, L. Zhang, T. J. Looney, B. Zhang, L. A. Godley, L. M. Hicks, B. T. Lahn, P. Jin, and C. He, *Nature biotechnology,* 2011, 29, 68-72.
5. M. Munzel, D. Globisch, and T. Carell, *Angewandte Chemie (International ed. in English),* 2011, 50, 6460-8.
6. B. Teague, M. S. Waterman, S. Goldstein, K. Potamousis, S. Zhou, S. Reslewic, D. Sarkar, A. Valouev, C. Churas, J. M. Kidd, S. Kohn, R. Runnheim, C. Lamers, D. Forrest, M. A. Newton, E. E. Eichler, M. Kent-First, U. Surti, M. Livny, and D. C. Schwartz, *Proceedings of the National Academy of Sciences of the United States of America,* 2010, 107, 10848-53.
7. M. Levy-Sakin and Y. Ebenstein, *Current Opinion in Biotechnology,* 2013, null.
8. R. K. Neely, J. Deen, and J. Hofkens, *Biopolymers,* 2011, 95, 298-311.
9. E. T. Lam, A. Hastie, C. Lin, D. Ehrlich, S. K. Das, M. D. Austin, P. Deshpande, H. Cao, N. Nagarajan, M. Xiao, and P.-Y. Kwok, *Nature biotechnology,* 2012, 30, 771-6.
10. Y. Michaeli and Y. Ebenstein, *Nature biotechnology,* 2012, 30, 762-3.
11. Y. Ebenstein, N. Gassman, S. Kim, J. Antelman, Y. Kim, S. Ho, R. Samuel, X. Michalet, and S. Weiss, *Nano Letters,* 2009, 9, 1598-1603.
12. S. Kim, A. Gottfried, R. R. Lin, T. Dertinger, A. S. Kim, S. Chung, R. A. Colyer, E. Weinhold, S. Weiss, and Y. Ebenstein, *Angewandte Chemie (International ed. in English),* 2012, 51, 3578-81.
13. J. M. Sidorova, N. Li, D. C. Schwartz, A. Folch, and R. J. Monnat, *Nature protocols,* 2009, 4, 849-61.
14. A. R. Hastie, L. Dong, A. Smith, J. Finklestein, E. T. Lam, N. Huo, H. Cao, P.-Y. Kwok, K. R. Deal, J. Dvorak, M.-C. Luo, Y. Gu, and M. Xiao, *PloS one,* 2013, 8, e55864.
15. C. E. Nestor, R. Ottaviano, J. Reddington, D. Sproul, D. Reinhardt, D. Dunican, E. Katz, J. M. Dixon, D. J. Harrison, and R. R. Meehan, *Genome research,* 2012, 22, 467-77.
16. A. Szwagierczak, S. Bultmann, C. S. Schmidt, F. Spada, and H. Leonhardt, *Nucleic acids research,* 2010, 38, e181.
17. W. Li and M. Liu, *Journal of nucleic acids,* 2011, 2011, 870726.
18. M. R. Branco, G. Ficz, and W. Reik, *Nature reviews. Genetics,* 2012, 13, 7-13.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method of labeling the epigenetic modification 5-hydroxymethyl-cytosine along a DNA molecule, the method comprising attaching to said DNA molecule a 5-hydroxymethyl-cytosine specific labeling agent, wherein said attaching comprises:
   subjecting 6-azidoglucose to an enzymatic catalysis by N-acetylhexoseamine 1-kinase (NahK) in the presence of ATP to thereby obtain a phosphorylated 6-azidoglucose;
   subjecting said phosphorylated 6-azidoglucose to enzymatic catalysis by uridyltransferase (GlmU) in the presence of UTP to thereby obtain UDP-6-$N_3$-Glucose;
   said UDP-6-N3-Glucose and β-glucosyltransferase, to thereby obtain a 5-hydroxymethyl-cytosine glycosylated by a 6-azidoglucose residue in said DNA molecule; and
   reacting said DNA molecule comprising said 5-hydroxymethyl-cytosine glycosylated by a 6-azidoglucose residue with a labeling agent derivatized by a reactive group which is chemically compatible with the azide group of said 6-azidoglucose residue.

2. The method of claim 1, wherein said labeling agent derivatized by said reactive group is a fluorescent labeling agent.

3. The method of claim 1, further comprising attaching to said DNA molecule an additional labeling agent distinct of said 5-hydroxymethyl-cytosine specific labeling agent.

4. The method of claim 3, wherein said additional labeling agent is a 5-methyl-cytosine specific labeling agent.

5. The method of claim 3, wherein said additional labeling agent is an epigenetic modification specific labeling agent.

6. The method of claim 3, wherein said additional labeling agent is a non-epigenetic modification specific labeling agent.

7. The method of claim 6, wherein said non-epigenetic modification specific labeling agent is a fluorescent agent which binds to nucleic acids.

8. The method of claim 1, not comprising subjecting said DNA molecule to fragmentation.

9. The method of claim 1, wherein said reactive group is an alkyne.

10. The method of claim 9, wherein attaching said labeling agent to said DNA molecule is effected by a click chemistry.

11. The method of claim 1, wherein said reacting is free of a copper catalyst.

12. The method of claim 1, wherein said DNA molecule is a genomic DNA molecule.

13. The method of claim 12, wherein said DNA molecule is longer than 20 Kb.

14. The method of claim 12, wherein said DNA molecule is longer than 40 Kb.

15. The method of claim 1, further comprising detecting the 5-hydroxymethyl-cytosine specific labeling agent.

16. The method of claim 15, wherein said detecting is effected in a high throughput setting of at least 300 DNA samples.

17. A method of in-situ imaging a DNA molecule, the method comprising:
   (a) attaching a 5-hydroxymethyl-cytosine specific labeling agent to said DNA molecule according to the method of claim 2; and (b) subjecting said DNA molecule to an imaging method suitable for detecting said 5-hydroxymethyl-cytosine specific labeling agent.

18. The method of claim 17, wherein said labeling agent is a fluorescent labeling agent said imaging method is a fluorescent imaging.

19. The method of claim 17, further comprising generating an optical image of said DNA molecule following said imaging.

* * * * *